United States Patent [19]

Bussey et al.

[11] Patent Number: 5,194,600

[45] Date of Patent: Mar. 16, 1993

[54] GENES WHICH PARTICIPATE IN β-GLUCAN ASSEMBLY AND USE THEREOF

[75] Inventors: Howard Bussey, Westmount; Charles Boone, London, both of Canada; Steve S. Sommer, Rochester, Minn.; Kathryn Hill, Montreal, Canada; Philip Meaden, Horsham, England

[73] Assignee: Royal Institute for the Advancement of Learning, Montreal, Canada

[21] Appl. No.: 488,316

[22] Filed: Mar. 5, 1990

[51] Int. Cl.$^5$ .............. C12Q 1/68; C12Q 1/02; C12P 21/04; C07H 19/06

[52] U.S. Cl. ................... 536/23.74; 435/6; 435/29; 435/71.1; 935/37; 935/69

[58] Field of Search .......... 435/320.7, 252.3, 1, 435/6, 29, 71.1; 536/69.1, 27, 7; 935/47, 48, 37, 69

[56] References Cited

U.S. PATENT DOCUMENTS 3,880,742  4/1975  James et al. ............... 495/200
4,810,646  3/1989  Jamas et al. ............... 435/101

OTHER PUBLICATIONS

Manners, D. J. et al., Biochem. J., 1973, 135: 19–30.
Manners, D. J. et al., Biochem. J., 1973, 135: 31–36.
Hutchins K. & Bussey, H. J. Bacteriol., 1983, 154: 161–169.
Roncero et al. J of Bact. 170(4): 1950 (1988).
Bonne Abs. Thesis disert. 51/09-B: 4144 (1989).

Primary Examiner—Robert A. Wax
Assistant Examiner—Miguel Escallon
Attorney, Agent, or Firm—Allegretti & Witcoff, Ltd.

[57] ABSTRACT

The present invention relates to DNA sequences coding for genes which participate in a yeast cell wall β-glucan assembly pathway. These genes are essential for normal cell growth and are tools which enable the 'in vitro' or 'in vivo' screening for differential inhibition of fungi pathogenic to plants and animals, including man by specific antifungal agents. Further, a method which allows one to produce structurally modified glucans by using the DNA sequences of the present invention is also provided. Such modified glucans can be used to facilitate protein extraction from a microorganism; as food additives or as immunomodulators. Also, a method for selecting yeast mutants resistant to killer toxins from other yeasts or fungi which comprises exposing sensitive yeast cells to such killer toxins on agar plates, and selecting for yeast cells that survived such exposure by their ability to grow and form colonies.

1 Claim, 1 Drawing Sheet

GENES WHICH PARTICIPATE IN β-GLUCAN ASSEMBLY AND USE THEREOF

BACKGROUND OF THE INVENTION

β-glucans, homopolymers of glucose, are an abundant class of polysaccharides that include cellulose, and appear to serve structural, functional and morphological roles at the cell surface of fungi, bacteria and plants. Despite their widespread occurrence, there has been surprisingly little work to address the basis of cell wall glucan biosynthesis at the genetic and molecular level in eukaryotes. 'In vitro' enzymatic reactions resulting in glucan synthesis have been defined and partially characterized for several systems though components of the synthetic machinery have eluded purification. The isolation of mutants defective in the production of cell wall glucan should define genes which encode biosynthetic enzymes as well as other products, for example those which regulate glucan synthesis or generate glucan precursors.

Mixed linked β-D-glucans consisting of glucopyranosyl residues joined through (1→3) and (1→6)-linkages are common to fungi belonging to the Ascomycetes, Basidomycetes and Oomycetes. Fractionation studies of the *Saccharomyces cerevisiae* cell wall demonstrated the presence of several glucan subclasses, which could be structurally distinguished by polymer length and the ratio of (1→3) to (1→6)-β-D-linkages. Much of the yeast cell wall glucan is isolated from whole cells as an alkali insoluble fraction which was found to contain two distinct types of polymers. The most abundant alkali insoluble glucan consists predominantly of repeating units of linear (1→3)-β-linked residues, 3% of which are branched through a (1→6)-β-linkage (Manners, D. J. et al., 1973, *Biochem. J.*, 135:19-30). This glucan has a degree of polymerization estimated to be about 1,500 and may determine the shape and stability of the yeast cell wall. The other alkali insoluble glucan has a degree of polymerization estimated to be about 140 and contains residues which are predominantly connected through linear (1→6)-β-linkages (Manners, D. J. et al., 1973, *Biochem. J.*, 135:31-36). This glucan will be referred to as (1→6)-β-glucan although in addition to linear (1→6) linked units, it is composed of some linear (1→3)-linked residues and a relatively high proportion of (1→3, 1→6)-linked branched residues (14%). Yeast (1→6)-β-glucan accounts for approximately 20% of the alkali insoluble glucan or 3% of the total cellular dry weight.

The K1 killer toxin of *S. cerevisiae* provides a selection scheme for the isolation of mutants defective in (1→6)-β-D-glucan production. This toxin is a protein secreted by killer yeast strains which kills sensitive (nonkiller) strains. K1 toxin displays a lectin-like affinity for linear (1→6)-β-D-glucan and must bind to the wall of sensitive yeast in order to initiate the killing process. Mutations in the so called KRE1 gene result in killer toxin resistance, and are associated with an abnormal production of cell wall (1→6)-β-glucan (Hutchins K. and Bussey, H., 1983, *J. Bacteriol.*, 154:161-169).

The KRE1 gene encodes a protein directed into the yeast secretory pathway. The (1→6)-β-glucan fraction which remained in a KRE1 mutant yeast strain had an altered structure with a smaller average polymer size, suggesting that (1→6)-β-glucan is synthesized in a stepwise manner.

Spiros J. et al. have described methods to produce glucan particles from *Saccharomyces cerevisiae* strains (U.S. Pat. No. 4,810,646 issued on Mar. 7, 1989). They have also demonstrated that there is a variation in viscosity profiles of yeast glucan depending upon the strain of *Saccharomyces cerevisiae* used. They used the following strains of *S. cerevisiae* A364A, 374, 377 and a mutant R4 which is characterized by its resistance to laminarinase. These methods to produce glucans from these strains are unrelated to the present invention.

At first, the mutant R4 appears to be related to the kre mutants of the present invention and are said to have an increased β-(1→6) glucan fraction. Glucan obtained from this mutant was shown to have an altered network-compression modulus versus volume fraction. On this basis, this mutant is said to give glucan matrices with altered structural properties, and in this general respect resembles the mutants defective in genes described in the application.

The mutant R4, although not characterised or described in detail, appears to be unrelated in properties to the kre mutants described in the present invention. The mutant R4 is said to have increased β-(1→6) glucan production, whereas we show that kre mutants have less. Further, the mutant R4 has resistance to laminarinase, while the kre mutants in contrast show an increased sensitivity to a functionally similar (1→3)-β-glucanase enzyme, zymolyase. In these respects, mutant R4 even though structurally altered in glucan, has different properties and characteristics from the kre mutants. The DNA sequence of the mutant R4 is not known. By not knowing the mutant R4 DNA sequence, one cannot study its mechanism of action and one is very limited in its application.

It would be highly desirable to know which gene products are required for fungal cell wall biosynthesis. These could be used as potential targets for the screening for specific antifungal agents which act against fungi pathogenic to plants and animals, including man. It would be of a great advantage to be able to selectively inhibit yeast cell growth without affecting mammalian or plant cells.

It would also be desirable to have the complete nucleic acid sequence of genes involved in the cell wall β-glucan assembly pathway. Such genes could, through recombinant DNA technology, be used to overproduce glucans, to produce modified glucans, and to produce microorganisms having modified cell walls to facilitate cell lysis for extraction of proteins and other molecules.

SUMMARY OF THE INVENTION

In accordance with the present invention, there are provided DNA sequences coding for genes which participate in a yeast cell wall β-glucan assembly pathway and their characterization to show that they, in fact, participate in the cell wall β-glucan assembly pathway.

Also, using the DNA sequences of the present invention, there is provided a method for the 'in vitro' screening for differential inhibition of fungi pathogenic to plants and animals, including man, by specific antifungal agents which comprises:

producing the corresponding gene product of the sequences or genes of the present invention; and to use said gene product as a tool for the screening of said antifungal agents which inhibit said fungi.

There is also provided, an enabling method for the 'in vivo' screening for differential inhibition of fungi pathogenic to plants and animals, including man by specific antifungal agents, which comprises:

producing a mutant containing the sequences or genes of the present invention; and to use said mutant for the differential screening of said antifungal agents which inhibit said fungi.

A method of structurally modifying yeast glucans which comprises deleting or altering any of the genes of the present invention in the genome of a yeast, whereby causing a mutation which causes the gene product or the glucan to be modified. Such modified glucans can be used to facilitate protein extraction from a microorganism; as food additives; and as immunomodulators. The modified glucans of the present invention can also be used to elicit the host defense response in plants.

Furthermore, there is provided a method for selecting yeast mutants resistant to killer toxins from other yeasts or fungi which comprises:

exposing sensitive yeast cells to such killer toxins on agar plates; and selecting for yeast cells that survived such exposure by their ability to grow and form colonies.

Further details concerning the present invention are disclosed in the following description.

IN THE DRAWINGS

FIGS. 1a and 2b shows a restriction map of an allelic C. albicans KRE1 functional homologs.

DETAILED DESCRIPTION OF THE INVENTION

In order that the invention herein described may be more fully understood, the following detailed description is set forth. In the description, the following terms are employed:

| Abbreviations of naturally occuring amino acids: | | | | | |
|---|---|---|---|---|---|
| Alanine | A | Ala | Leucine | L | Leu |
| Arginine | R | Arg | Lysine | K | Lys |
| Asparagine | N | Asn | Methionine | M | Met |
| Aspartic acid | D | Asp | Phenylalanine | F | Phe |
| Cysteine | C | Cys | Proline | P | Pro |
| Glutamic acid | E | Glu | Serine | S | Ser |
| Glutamine | Q | Gln | Threonine | T | Thr |
| Glycine | G | Gly | Tryptophan | W | Trp |
| Histidine | H | His | Tyrosine | Y | Tyr |
| Isoleucine | I | Ile | Valine | V | Val |

In accordance with the present invention, there is provided the DNA sequence of two Saccharomyces cerevisiae genes called KRE1 and KRE5, which both participate in a yeast cell wall $\beta$-glucan assembly pathway. These DNA sequences or fragments thereof can be used as either a method for the 'in vitro' or 'in vivo' screening for specific antifungal agents directed against fungi pathogenic to plants and animals, including man; or as a method which allows one to produce structually modified glucans to be used as food additive, immunomodulators or to facilitate protein extraction from yeast.

The Saccharomyces cerevisiae KRE1 gene encodes a Ser/Thr rich protein, that is directed into the yeast secretory pathway, where it is highly modified, probably through addition of O-linked mannose residues. Gene disruption of the KRE1 locus leads to a 40% reduced level of cell wall $(1\rightarrow 6)$-$\beta$-glucan. Structural analysis of the $(1\rightarrow 6)$-$\beta$-glucan fraction, isolated from a strain with a kre1 disruption mutation, showed that it had an altered structure with a smaller average polymer size. Mutations in two other loci, KRE5 and KRE6 also lead to a defect in cell wall $(1\rightarrow 6)$-$\beta$-glucan production and appear to be epistatic to KRE1.

The S. cerevisiae KRE5 encodes a large hydrophilic secretory glycoprotein which contains the COOH-terminal endoplasmic reticulum (ER) retention signal -HDEL (i.e. His-Asp-Glu-Leu). Deletion of the KRE5 gene resulted in cells with aberrant morphology and extremely compromised growth. Second site suppressors to the KRE5 deletions permitted an analysis of the deletion strains which were found to contain no alkali-insoluble $(1\rightarrow 6)$-$\beta$-D-glucan. These results indicate a role for $(1\rightarrow 6)$-$\beta$-D-glucan in normal cell growth, and outline a pathway for sequential assembly of yeast cell wall $(1\rightarrow 6)$-$\beta$-D-glucan.

KRE1 and KRE5 Gene

KRE1 and KRE5 have been isolated, characterized and sequenced according to the following procedures.

Yeast Strains and Procedures

Yeast strains used in this work are presented in Table I. Growth conditions and media (YEPD which contains yeast extract, peptone and dextrose, complete and Halvorson's) were as described previously by H. Bussey et al. (1982, Mol. Cell. Biol., 2:346-354) and R. Wickner (1978, Genetics, 88:419-425). Standard techniques were used for diploid construction and sporulation (Sherman, F. et al., 1982, Methods in yeast genetics, Cold Spring Harbor Lab., N.Y.). Transformation was performed using the lithium acetate technique of H. Ito et al., (1983, J. Bacteriol., 153:163-168).

TABLE I

YEAST STRAINS

| Strain | Genotype | Source |
|---|---|---|
| S484 | a ura1 met13 can1 cyh2 mkt1 [HOK] [NEX] | 1 |
| S486 | a ura1 met13 can1 cyh2 mkt1 [HOK] [NEX] | 1 |
| S442 | α lys2 cyh2 can1 mkt1 [HOK] [NEX] | 1 |
| TA405 | a/α his3/his3 leu2/leu2 can1/can1 | 2 |
| 463-1A | α kre1::HIS3/his3 leu2 | This work |
| 463-1B | α kre1::HIS3/his3 leu2 | This work |
| 463-1C | α KRE1 leu2 his3 | This work |
| 463-1D | α KRE1 leu2 his3 | This work |
| 11A | α kre1 ura3 | This work |
| T158C/S14a | a/α his4c-864/his4 ade2-5/ADE2 [KIL-K1] | 3 |
| HAB150-1 | a/α kre1-3/kre1::HIS3 his3/HIS3 leu2/LEU2 lys2/LYS2 | This work |
| 7B | α glc1 his3 ura3 | This work |
| S726 | a kre5-1 lys2 cyh2 can1 mkt1 [HOK] [NEX] | This work |
| S731 | a kre6-1 lys2 cyh2 can1 mkt1 [HOK] [NEX] | This work |
| HAB105a-2C | a kre5-1 ura3 | This work |
| YDK5,7,9,11,16 | a/α kre5Δ1::HIS3/KRE5 leu2/leu2 can1/can1 his3/his3 | This work |

TABLE I-continued
YEAST STRAINS

| Strain | Genotype | Source |
|---|---|---|
| YDK5/1A | α leu2 his3 kre5Δ1::HIS3 | This work |
| YDK5/1B | α leu2 his3 kre5Δ1::HIS3 | This work |
| YDK5/2D | α leu2 his3 kre5Δ1::HIS3 | This work |
| YDK5/3B | α leu2 his3 kre5Δ1::HIS3 | This work |
| YDK5/3C | α leu2 his3 kre5Δ1::HIS3 | This work |
| YDK5/1C | α leu2 his3 KRE5 | This work |
| K5D4 | a/α leu2/leu2 his3/HIS3 lys2/LYS2 kre5Δ1::HIS3/kre5 | This work |
| T9-3C | a ura3 leu3 his3 | 2 |
| HAB 224-2C | kre6-1 ura3 | This work |
| HAB 223-2B | kre5-1 met13 | This work |
| HAB 225-18A | KRE5 KRE6 | This work |
| HAB 225-18B | kre5-1 kre6-1 | This work |
| HAB 225-18C | kre5-1 kre6-1 | This work |
| HAB 225-18D | KRE5 KRE6 | This work |
| HAB 228 | a/α ade2/ADE2 his3/HIS3 kre5-1/KRE5 ura1/ura1 met13/MET 13 | This work |
| HAB 230-10C | a kre5-1 his3 ura3 can1 | This work |
| X1095-7C | a cyh4 ade2 ade8 his3 trp1 | Yeast Genetic Stock Center, CA |
| 212-244-1A | α glc1 | Yeast Genetic Stock Center, CA |

1- Ridley, S. P. et al., 1984, Mol. Cell. Biol., 4:761-770;
2- Whiteway, M. and Szostak, J. W., 1985, Cell, 43:483-492;
3- Bussey, H. et al., 1979, J. Bacteriol., 140:888-892.

All strains generated in this work are obtained from genetic manipulation of the strains referenced in the above table.

(1→6)-β-Glucan Quantification

The following procedure was used to measure the quantity of (1→6)-β-glucan.

Yeast cells were grown as 5-10 ml cultures in YEPD or minimal media (if plasmid selection was required) until stationary phase. Cells were harvested, washed once with distilled water and then extracted 3× with 0.5 ml of 3% aqueous solution of NaOH at 75° C. (1 hour per extraction). Following alkali extraction, the cells were washed once with 1 ml of 100 mM Tris-HCl, pH 7.5, and once with 1 ml of 100 mM Tris-HCl, pH 7.5, and once with 1 ml of 10 mM Tris-HCl, pH 7.5. The washed cells were then digested for 16 hours at 37° C., with 1 mg of Zymolyase 100,000 ® (ICN Biomedicals, Inc., Costa Mesa, Calif.), in 1 ml of 10 mM Tris-HCl, pH 7.5. Approximately 90% of the glucose-containing carbohydrate was released into the supernatant by this digestion. It is known that the enzyme Zymolyase ® does not contain a (1→6)-β-glucanase activity (Hutchins, K. and Bussey, H., 1983, J. Bacteriol., 154:161-169). The insoluble pellet which remains after the zymolyase digestion, was removed by centrifugation, and the supernatant was dialyzed against distilled water, using Spectra/Por ® tubing with a 6,000-8,000 Mol. wt. cut off (Spectrum Medical Industries, Inc., Los Angeles, Calif.), for 16 hours. The total yield of glucan was determined by the sum of the carbohydrate content of both the zymolyase insoluble pellet and the solubilized supernatant before dialysis. Analysis of the carbohydrate content of the retained fraction after dialysis determined the proportion of (1→6)-β-glucan. Total carbohydrate of each fraction was measured as hexose by the borosulfuric acid method as described by Badin, J. et al. (1953, Proc. Soc. Exp. Biol. Med., 84:288-291).

Plasmids

The following plasmids were used in the cloning, the sequencing and the manipulation of these genes and their fragments. Most of them are standard vectors which are readily available.

Vector YCp50 containing the yeast genomic library is as described by Rose, M. D. et al. (1987, Gene, 60:237-243). Plasmid pFL44 is a 2μ based, multicopy, yeast shuttle vector with URA3 and Ap$^r$ markers, which contains the pUC19 polylinker. The plasmid pFL44 was used for subcloning DNA fragments of YCp50:KRE1. Bluescript+ and Bluescript− vectors (Strategene; San Diego, Calif.) were used for various recombinant DNA constructions and for production of single stranded DNA. Plasmids pBR322, pUC19 and M13mp19 were also used for producing single stranded DNA. The yeast expression vector, PVT100U, contains the f1 origin of replication, also allowing the production of single stranded DNA, and was provided by T. Vernet et al. (1987, Gene, 52:225-233). Plasmid PBSK:HIS3 was created by ligating a 1.7 kb BamHI fragment containing the HIS3 gene (Struhl, K., 1985, Nucleic Acids Res., 13:8587-8600) into Bluescript+. Another Bluescript+ based plasmid, p486, contains the 0.5 kb EcoRV-HincII fragment of KRE1 ligated into these restriction sites of the Bluescript polylinker. Plasmid p492 contains the 0.4 kb SpeI-NsiI fragment which spans the end of the KRE1 open reading frame, ligated into the Spe1 and PstI sites of the Bluescript+ polylinker. Plasmid p143 was constructed from Bluescript− through ligation of the 2 kb NheI-PstI fragment of the KRE1 locus into the Spe1-PstI digested vector. Plasmid p339 was derived from PUC19 and contains a modified BamHI-SalI fragment (containing the prepro-α factor structural gene) from pJK6 (Kurjan, J. and Herskowitz, I., 1982, Cell., 30:933-943) ligated into the polylinker. The modification concerns the insertion of a BglII restriction site (5'-AGATCT-3') six nucleotides prior to the initiation codon of prepro-α factor (Kurjan, J. & Herskowitz, I., 1982, Cell., 30:933-943).

DNA Purification and Recombinant DNA Techniques

Plasmid DNA purified from E. coli as described by T. Maniatis et al. (1982, Mol. Cloning, Cold Spring Harbor Lab., New York). Yeast DNA was isolated according to R. W. Davis et al. (1980, Meth. Enzymol., 65:404-411). Restriction endonucleases, T4 DNA polymerase, T4 DNA ligase and Klenow fragment were purchased from either Bethesda Research Laboratories, Inc. (Gaithersburg, Md.) or New England Laboratories, Inc. (Beverly, Mass.) and were used as recommended by the suppliers. Southern Blot hybridization and nick translations were carried out either as described by A. Dmochowska et al. (1987, *Cell*, 50:573–584) or using the non-radioactive DNA detection kit of Boehringer Mannheim (Indianapolis, USA). Oligonucleotide-directed mutagenesis was carried out according to T. A. Kunkel (1985, *Proc. Natl. Acad. Sci. USA*, 82:488–492) using the Mutagene ® 'in vitro' mutagenesis system (Bio-Rad).

DNA Sequencing a) KRE1:

Subclones of the KRE1 yeast genomic DNA were made in Bluescript vectors or in PVT100U. Plasmids containing subclones were transformed into the bacterial strain, UT580, and single stranded DNA was made using M13K07 helper phage (Vernet, T. et al., 1987, *Gene*, 52:225–233). Sequencing was by the dideoxy method (Sanger, F. et al., 1977, *Proc. Natl. Acad. Sci. USA*, 74:5463–5467) and was determined for both strands, using the Sequenase Kit ® (US Biochemicals, Cleveland, Ohio) with [$\alpha$-$^{35}$S]dATP (Amersham Canada Ltd, Oakville, Ont.) as a substrate. DNA primers were either Bluescript-specific primers or synthesized to be complementary to parts of the KRE1 DNA sequence.

b) KRE5:

Subclones of KRE5 for sequencing were made in the Bluescript vectors or M13mp19. Deletions of DNA subclones were prepared in M13 by the method of Dale, R. M. K. et al. (1985, *Plasmid*, 13:31–40). Bacterial strains UT580, using M13K07 (Vernet, T. et al., 1987, *Gene*, 52:225–233), JA221 (Clarke, L. and Carbon, J., 1978, *J. Mol. Biol.*, 120:517–532), and JM103 (Messing et al., 1981, *Nuc. Acids Res.* 9:309–321) were used for transformation and production of single stranded DNA. The sequencing was by the dideoxy method of F. Sanger et al. (1977, *Proc. Natl. Acad. Sci. USA*, 74:5463–5467) using the Sequenase kit ® (U.S. Biochemicals, Cleveland, Ohio) and [$\alpha$-$^{35}$S]dATP as a substrate. DNA primers were either the Bluescript Universal or reverse primers or those synthesized to be complementary to parts of the KRE5 sequence.

Mapping a) KRE1:

The diploid HAB150-1 (kre1-3/kre1::HIS3) was sporulated for tetrad analysis, 22 tetrads of 23 were parental ditype for killer resistance and one was a tetratype. These results show that the cloned sequence is tightly linked to the KRE1 locus. In further experiments, we have determined the location of KRE1 on the yeast genetic map.

A southern blot of chromosomes separated by pulse field electrophoresis (Carle, G. F. and Olson, M. V., 1985, *Proc. Natl. Acad. Sci. USA*, 82:3756–3760) was probed with KRE1 DNA. The KRE1 sequence hybridized to chromosome XIV. Tetrad analysis provided the following linkage for KRE1: the kre1-pha2 map distance is 8 cM (41 parental ditypes [PD], 0 nonparental ditypes [NPD] and 8 tetratypes [TT], the kre1-met2 map distance is 34 cM (34 PD, 1 NPD, and 56 TT), the kre1-pet2 map distance is 48 cM (12 PD, 2 NPD and 27 TT). Of 7 tetrads examined where kre1 was recombinant with pha2, 5 tetrads were also recombinant for kre1 with met2 and pet2, suggesting the order kre1 pha2 met2 pet2. The map distances were calculated according to Mortimer R. K. and Schild D. (1985, *Microbiol. Rev.*, 99:181–212).

b) KRE5:

The location of KRE 5 on the physical genomic map was also determined. A 3.5 kb EcoR1-BamH1 fragment of the KRE5 gene was found to hybridise to chromosome XV by O-PHAGE blot.

Preparation of Glucanases

Crude glucanase (a mixture of endo-$\beta$-D-(1$\rightarrow$3) and $\beta$-D-(1$\rightarrow$6) activities) and non-lytic $\beta$-D-(1$\rightarrow$6)-glucanase were prepared from *Bacillus circulans* WL-12 (obtained from Rombouts et al., 1978, *Carbohydr. Res.*, 64:237–249). Crude glucanase was concentrated 500 fold from culture supernatants of *B. circulans* by ultrafiltration through an Amicon YMS ® membrane and dialyzed against 50 mM sodium phosphate (pH 7.0) using Spectra/Por ® 6,000–8,000 Mol. wt. cut off. The non-lytic $\beta$-D-(1$\rightarrow$6)-glucanase was purified from the crude material by Sephadex G100 ® chromatography as described by Rombouts et al. (1978, *Carbohydr. Res.*, 64:237–249). After pooling and concentrating the fractions containing $\beta$-D-(1$\rightarrow$6) -glucanase, residual $\beta$-D-(1$\rightarrow$3)-glucanase activity was removed by passing the enzyme down a column containing a 2:1 (v/v) mixture of Bio-Gel P-2 ® (Biorad) and alkali-insoluble glucan from YDK5/3B. Phosphate buffer was used for elution. Conditions for digestion with the non-lytic $\beta$-D-(1$\rightarrow$6)-glucanase were as described by Rombouts et al. (1978, *Carbohydrates Res.*, 64:237–249).

Polysaccharide Analysis of Hydrolysed Glucan

Yeast was grown to stationary phase in complete medium (10 ml) containing 500$\mu$Ci[$^3$H]-glucose (Amersham). Alkali-insoluble glucan was prepared and exhaustively digested with zymolyase (2 mg ml$^{-1}$, 10 mM Tris-HCL, pH 7.5) and 200 $\mu$l crude glucanase from *B. circulans*. The soluble carbohydrate was separated on a Bio-Gel P-2 ® column (Biorad, 85×1.2 cm), using 0.1N acteic acid as eluent. Fractions containing disaccharide were pooled, concentrated by lyophilisation, and analyzed by thin layer chromatography (Silcagel 60 ®, Merck) using butanol/acetate/water (40:50:10 v/v) as solvent. Sugars were visualized by staining with silver nitrate. Areas corresponding to laminaribiose (Sigma) maltose and gentiobiose (Sigma) were cut from the thin layer plate and quantitated by liquid scintillation counting. For the wild type, YDK5/1C (KRE5), radiolabelled laminaribiose (13,404 cpm) and gentiobiose (7,381 cpm) could be detected. For the disruptant, YDK5/3B (kre5Δ1::HIS3), no radioactivity associated with gentiobiose was detected despite an approximately three fold increase in sample loading. However, radiolabelled laminaribiose was detected at predicted levels (38,807 cpm).

Part a) KRE1

Cloning the Yeast KRE1 Gene

Strain 11A was transformed with a YCp50 based yeast genomic library (Rose, M. D. et al., 1987, *Gene*, 60:237–243) and uracil prototrophs were selected. Transformants were replica plated to minimal media, Halvorson's 1X pH 4.7 agar, which had been seeded with 75 $\mu$l/liter of a stationary culture of the diploid killer strain T158C/S14a and contained 0.002% of the vital stain methylene blue. Following replica plating, the methylene blue plates were incubated at 18° C. for three to four days; at the end of this period, the Kre+ transformants had stained a dark blue colour while kre− colonies remained white. Individual cells were isolated from the blue staining colonies and these were later grown up for plasmid recovery.

Two independent Kre+ transformants were obtained and found to be unstable for both the Kre+ and Ura+ phenotypes when grown under nonselective conditions in YEPD. A unique plasmid was isolated from each of these tranformants that could complement the kre1-1 mutation. One plasmid, YCp50:KRE1, contained a 6.5 kb insert of yeast genomic DNA and restriction endonuclease mapping revealed that this DNA fragment was contained within a large (11 kb) insert of the other complementing plasmid. Genetic analysis showed that the complementing fragment contained the KRE1 locus.

Nucleotide Sequence of KRE1

Subcloning of the insert of plasmid YCp50:KRE1 determined that a 3.9 kb BamHI-PstI restriction fragment could complement the kre−, phenotype of strain 11A. However, subclones on either side of an internal KpnI site failed to complement, suggesting that the KpnI site is located within the KRE1 functional region. Further subcloning experiments localized the complementing activity to a 1.5 kb NheI-NsiI fragment, the DNA sequence of this fragment shown in Table II was determined using the dideoxy nucleotide method of F. Sanger et al. (1977, *Proc. Natl. Acad. Sci. USA*, 74: 5463–5467). This sequence contains a single extended open reading frame which spans the KpnI site. This open reading frame would encode a protein of 313 amino acids with a molecular weight of 32,138Da.

The protein, Kre1p, displays a striking abundance of threonine (25%) and serine (15%) residues. The amino-terminus of Kre1p is hydrophobic and resembles the signal sequences of secreted proteins. There are two potential signal cleavage sites (von Heijne G., 1984, *J. Mol. Biol.*, 173: 243–251) found after amino acid residues 23 and 27 (Table II). The last twenty-one amino acid residues of Kre1p also form a hydrophobic sequence. No sites for N-linked glycosyl attachment were observed, however, the abundance of serine and threonine residues may provide sites for O-linked glycosylation (Tanner, W. and Lehle, L., 1987, *Biochim. Biophys. Acta.*, 906: 81–99). Kre1p contains an internal repeat of fifteen amino acids. Comparison of both the KRE1 nucleotide sequence, and the deduced primary amino acid sequence with those from available data bases has not revealed any sequences with significant similarities to KRE1.

TABLE II

KRE-1 sequence

```
          NheI
          GCTAGCAGTTATTTCACTTTCATTTACAGCATCCCTCATGTTTATTATCTCTTTATCTAATATAAATTAGGAACTAAATAAT  -360

CCCCTCACCGTATAAAGGCGACAGTTCCGTGACGGTTACTATTATGAATATCTCAACGGAA

AGAGGGCATTAAAAGATCATAAATAGTTGGTACTCTCGTATTTTATATATATACACT  -240

ATATTTAACACTTTTACTGCTCAATTGTGCCATATACTTCGCCTTATTGCGTACATTCT

EcoRV
                                          TCACCTTGTATCCCCTACCTCAGCGTGTATGGTGATATCGCGTTTTTCATAAACTGA  -120

GAATGGGGCTTTTTCTATAACGTGTATTATGAAAAAGAAAATAAAAATCAAGAATTAA

GCACTTGTATGCTACAGTAAAGACCTCTTCAACTTCTGCAAGACAATCAAAAAAAAA   -1

▽             •
ATG ATG CGT CGC ACG CTA TTA CAT TCA TTC GCT ACG CTG CTT TCT TTG TCG TGG TCA GCT ATG GTC GCG GTG ACA ACT   90
Met Met Arg Arg Thr Leu Leu His Ser Phe Ala Thr Leu Leu Ser Leu Ser Trp Ser Ala Met Val Ala Val Thr Thr   30

CAG GTT ACA GTG GTA ACA AAT GTC GCA GGG GCC CTG GTT ACG GAG GAC CCT GCC ACC GCT GCT GCT ACA GCT ACA ACT  180
Gln Val Thr Val Val Thr Asn Val Ala Gly Ala Leu Val Thr Glu Asp Pro Ala Thr Ala Ala Ala Thr Ala Thr Thr   60

HincII
ACC GCT CAA ACA GGT TTC TTC ACT GTA TTC ACT ACC ACT AAC GAT GTC GGA ACC GTC CTT ACT CAG ACA GTC AAC AGA GCC  270
Thr Ala Gln Thr Gly Phe Phe Thr Val Phe Thr Thr Thr Asn Asp Val Gly Thr Val Leu Thr Gln Thr Val Asn Arg Ala  90

ACT ATG CTA CCA ACC ACG ACT ACT TCT ACT TCT GGT AAG ACA ACC ACT GTT ACA ACT CCT ACC GCA ACT TCA TCG TTG TCT TCG GGA  360
Thr Met Leu Pro Thr Thr Thr Ser Thr Ser Gly Lys Thr Thr Thr Val Thr Thr Pro Thr Ala Thr Ser Ser Leu Ser Ser Gly  120

KpnI
CTG TAT TTA TCT ACA GTT ACC GGT ACC ACA AAC GAT TTG GGT ACC ACA GTT ACA TTG ACT CAA CAA GTT ACA CAT TCT AGC ACC AGT GCT ACT  450
Leu Tyr Leu Ser Thr Val Thr Gly Thr Thr Asn Asp Leu Gly Thr Thr Val Thr Leu Thr Gln Thr Val Thr His Ser Ser Thr Ser Ala Thr  150

TCA TCC GCC TCC TCG TCT GTG TCC TCT TCG TCT GGT TCA TCC AGT GTA AAG ACG ACA GGG AGC GCA GTA  540
Ser Ser Ala Ser Ser Ser Val Ser Ser Ser Ser Gly Ser Ser Ser Val Lys Thr Thr Thr Gly Ser Ala Val  180

SpeI
GCT GAA ACA GGC ACC AGG CCA GAC CCC TCC ACA GAC TTC ACA GAA CCT GTG TCT GCT GTC ACT AGT CTA ATT GAC TCA TAC ATT  630
Ala Glu Thr Gly Thr Arg Pro Asp Pro Ser Thr Asp Phe Thr Glu Pro Val Ser Ala Val Thr Ser Leu Ile Asp Ser Tyr Ile  210
```

TABLE II-continued

KRE-1 sequence

```
ACC ATC ACT GAA GGT ACA ACC TCC ACT TAC ACA ACC ACA CGT GCG CCA ACG TCC ACT GTT GTT AGA CAG GGC AAC ACT ATC      720
Thr Ile Thr Glu Gly Thr Thr Ser Thr Tyr Thr Thr Thr Arg Ala Pro Thr Ser Thr Val Val Arg Gln Gly Asn Thr Ile      240
                                                                SnaBI
ACT GTG CAA ACT ACT TTT GTC CAG CGT TTC TCC TCC CAG GTA ACA GTC ACA GCT TCT CCC GTG GGG TCT ATT GGG ATG GGT ACT TTA   810
Thr Val Gln Thr Thr Phe Val Gln Arg Phe Ser Ser Gln Val Thr Val Thr Ala Ser Pro Val Gly Ser Ile Gly Met Gly Thr Leu  270

ACC GGT ACT GTA GGC GTT ATT AAA TCT GCA ATA AAG AAA ACA GTT TCG CAT AAT GAG GCC CAG CAT CTA GGT ATG AGT TCG TTT ACT TCA   900
Thr Gly Thr Val Gly Val Ile Lys Ser Ala Ile Lys Lys Thr Val Ser His Asn Glu Ala Gln His Leu Gly Met Ser Ser Phe Thr Ser  300

ATT TTG GGT GGG CTA TTA ACG GTT TTA ATT TGG TTC TTA TAA ATTTTTATTCAGAAATAAACACAAACATATACATATAAGAGTAAAAATAAAAAATAAAAA   1005
Ile Leu Gly Gly Leu Leu Thr Val Leu Ile Trp Phe Leu                                                                 313
                                                                                    NsiI
AATTTTTACAGGGTTAAAAATAAAGAAAAACCATCACTCCTTTCTATTTCATAATCCATGACAAACTTGATGCAT                                        1079
```

Arrows show the position of the predicted signal cleavage sites determined by using the rules of G. von Heijne (1984, *J. Mol. Biol.*, 173: 243-251). A 15 amino acid direct repeat is underlined by a dashed line. The carboxy-terminal hydrophobic sequence of the KRE1 gene product is underlined by a continuous line. Asterisks show the positions of restriction sites inserted using site specific mutagenesis. Various restriction sites used for recombinant DNA constructs are designated above the DNA sequence.

The KRE1 Gene Encodes a Product with a Functional Signal Peptide

Restriction endonuclease sites were introduced three nucleotides prior to, and immediately after, the KRE1 open reading frame using site specific mutagenesis. Introduction of these new sites facilitated the ligation of the open reading frame into a 2μ based expression vector, pVT100U, which contains the ADH1 promoter and terminator (Vernet et al., 1987, *Gene*, 52: 225-233). Upon transformation of a kre1-1 mutant, the resultant plasmid, pVT:KRE1, fully complemented the kre− phenotype and led to (1→6)-β-glucan levels equivalent to those induced by YCp50:KRE1 (Table III). Transformation of a wild type (Kre1+) strain with pVT:KRE1 did not lead to an increased amount of (1→6)-β-glucan.

TABLE III

| Plasmid dependent maturation of cell wall (1→6)-β-glucan | | |
|---|---|---|
| Yeast Strain (Allele at KRE1 locus) | Transformation Plasmid | (1→6)-β-glucan μg/mg dry wt. |
| 11A (kre1-1) | YCp50 | 15.7 ± 1.4 |
| 11A (kre1-1) | YCp50:KRE1 | 41.4 ± 4.7 |
| 11A (kre1-1) | pVT100U | 17.5 ± 1.1 |
| 11A (kre1-1) | pVT:KRE1 | 42.6 ± 4.1 |
| 7B (KRE1+) | pVT100U | 38.9 ± 3.9 |
| 7B (KRE1+) | pVT:KRE1 | 45.2 ± 6.4 |

Yeast (1→6)-β-glucan levels were analyzed for various 11A (kre-1-1, ura3) transformants. Plasmid YCP50:KRE1 contains a yeast genomic insert that complements the kre1-1 mutation ligated into the centromeric (single copy) vector YCp50. Plasmid pVT:KRE1 contains the KRE1 open reading frame ligated into the 2μ derived (multi copy) expression vector pVT100U. Transcription of the KRE1 from pVT:KRE1 occurs via the ADH1 promoter. Yeast (1→6)-β-glucan levels were also analyzed for transformants of strain 7B (ura3, his3, glc1). Error represents one standard deviation.

To determine whether the KRE1 sequence encoded a functional signal peptide, a deletion was made of the first 72 nucleotides of the open reading frame (predicted to encode 24 N-terminal amino acids of Kre1p). The resultant construct was introduced into pVT100U, positioning Met 25 of Kre1p next to the ADH1 promoter. When transformed into yeast cells mutant at the KRE1 locus, the leader deleted construct (pVT:Δ24/KRE1) did not complement the kre− phenotype. However, if the leader deleted portion of the KRE1, sequence was replaced with a segment of DNA which encodes the first 20 amino acids of the alpha factor precursor (Kurjan, J. and Herskowitz, I., 1982, *Cell*, 30: 933-944) (pVT:a20/KRE1), a Kre+ phenotype was observed.

Part b) KRE5

Isolation of the KRE5 Gene

The wild type KRE5 gene was isolated by functional complementation of the kre5 mutation. HAB105a-2C (kre5-1, ura3) was transformed with a yeast DNA library prepared in the centromeric vector, YCp50, which carries the URA3 gene as a selectable marker (Rose, M.D. et al., 1987, *Gene*, 20: 237-243). Uracil prototrophs were screened for a killer sensitive phenotype (kre+) as described for KRE1 above. One transformant from this screen was found to be completely sensitive to killer toxin in the seeded plate assay. Plasmid DNA, pKRE5, isolated from the transformant, was shown to transform HAB105a-2C to killer sensitivity and restore glucan content to wild type levels (38.1+/−1.6 μm-1 dry wt.). The cloned DNA fragment contained within pKRE5 was 5.8 kb in length. Several subclones of the 5.8 kb insert were constructed; each was unable to complement the kre5-1 mutation indicating that the KRE5 functional region spanned a substantial portion of the insert.

An allelism test indicated that this fragment was closely linked to the kre5-1 mutation and that we had cloned the KRE5 gene.

Nucleotide sequence of pKRE5

The nucleotide sequence of pKRE5 was determined using the dideoxy method of F. Sanger et al. (1977, *Proc. Natl. Acad. Sci. USA*, 74: 5363-5467). One long open reading frame of 4098bp was found within the insert. This open reading frame would encode a protein of 1365 amino acids with a molecular weight of 156 307 Da. A hydropathy profile of the predicted KRE5 gene product, Kre5p, indicated a hydrophilic protein with only one hydrophobic region located at the $NH_2$-terminus. This $NH_2$-terminal region has features characteristic of a signal sequence and three potential cleavage sites for signal peptidase with cleavage after amino acid 17 being the most favoured (von Heijne, G., 1984, *J. Mol. Biol.*, 173: 243-251). It is likely, therefore, that the Kre5p enters the secretory pathway. Thirteen potential sites for N-linked glycosylation, as predicted by the sequence Asn-X- Thr/Ser, were found throughout the sequence. The sequence, His-Asp-Glu-Leu (HDEL) was observed at the COOH-terminus of KRE5p. This sequence is thought to be a retention signal for soluble proteins resident in the endoplasmic reticulum (ER) of yeast (Pelham et al., 1988, *EMBO J.*, 7: 1757-1762). The amino acid sequence of KRE5 was compared to sequences in the European Molecular Biology Laboratory, Genbank, and National Biomedical Research Foundation protein databases; no significant homology to other sequences was observed.

TABLE IV

KRE5 sequence

```
-77 TATATAACGTGGCATATTAAAGATTAATTGTCCTGGTAGAATATAGACGTATCAGTGTGAGTGCCTCTGTTGATTTA

1 ATGAGACTACTTGCGTTGGTATTGTTATTGTTGTGTGCGCCGCTTCGTGCATGGACTTATAGCTTA
  1  M  R  L  L  A  L  V  L  L  L  L  C  A  P  L  R  A  W  T  Y  S  L

CGATATGGCATACCCGAATCTGCTCAGGTCTGGTCTATTTTAGTTCATTTACTG
     R  Y  G  I  P  E  S  A  Q  V  W  S  I  L  V  H  L  L
```

TABLE IV-continued
KRE5 sequence

```
121  GGCGATGTTGATAATCAGCTGTTAACTAATTTATATCCTTTGGTTACCGGTTTGGATGACGAGATT
 41   G  D  V  D  N  Q  L  L  T  N  L  Y  P  L  V  T  G  L  D  D  E  I

GTATTTCAAGAAAATCTTGTGGCGCTAACTTCCAATGTATTAAGGGAGCGATAC
               D  I  Q  E  N  L  V  A  L  T  S  N  V  L  R  E  R  Y

241  GATAAAGAGGATGTGGCTGATTTATTGGAACTGTATGCTAGTCTTTACCCTATGGGTATGATACAG
 81   D  K  E  D  V  A  D  L  L  E  L  Y  A  S  L  Y  P  M  G  M  I  Q

CACGATATCAGTTCCAATGCAGAACAAGACGATGCAAATAGTAGCTATTTCGTT
               H  D  I  S  S  N  A  E  Q  D  D  A  N  S  S  Y  F  V

361  TTGAATGGTAATAGGTACGAAAAGCCCGACGACGTGTTCTACTTGAAATCTAAGGATTTAACAAT
121   L  N  G  N  R  Y  E  K  P  D  D  V  F  Y  L  K  S  K  D  L  T  I

CAACAGAAAGTCCCAGATGTTGATGTTATACAACCTTACGATGTTGTCATTGGT
               Q  Q  K  V  P  D  V  D  V  I  Q  P  Y  D  V  V  I  G

481  ACTAACTCAGAAGCGCCGATATTGATCTTGTACGGTTGTCCTACCGTTATTGACTCCGACTTCGAA
161   T  N  S  E  A  P  I  L  I  L  Y  G  C  P  T  V  I  D  S  D  F  E

GAATTCAATAGGAATTTATTTATGGAAGCAATGAATGGAGAGGGAAAATTTAGA
               E  F  N  R  N  L  F  M  E  A  M  N  G  E  G  K  F  R

601  TTATTTTGGAGATCCACATGTTCCCTTGATGGGAAAAGCGTGGAGTATCCCTTAACTCATCCGCTT
201   F  I  W  R  S  T  C  S  L  D  G  K  S  V  E  Y  P  L  T  H  P  L

GAAATTACTTTACAAAATGGTTCTAGAATGAGCTCCATACCTCAATTAAAAAAA
               E  I  T  L  Q  N  G  S  R  M  S  S  I  P  Q  L  K  K

721  ATACTATATACTGTACCCAAAGAAATATTGGTTGGAGCAGACAACGATGATCAGCTCCATGATCTA
241   I  L  Y  T  V  P  K  E  I  L  V  G  A  D  N  D  D  Q  L  H  D  L

GAACCAGAAGAATTACGTGAACTTGATTTGAGAGTAACATCGTTAATCTCAGAA
               E  P  E  E  L  R  E  L  D  L  R  V  T  S  L  I  S  E

841  TTTTACCAATATAAAAAGGATATCACAGCCACTCTAAATTTCACCAAAAGTATTGTTAACAACTTT
281   F  Y  Q  Y  K  K  D  I  T  A  T  L  N  F  T  K  S  I  V  N  N  F

CCACTAATCTCTAAACAACTGATTAAGGTTTCATCTGTTAACAAGGATATAATA
               P  L  I  S  K  Q  L  I  K  V  S  S  V  N  K  D  I  I

961  ACAAGTAATGAAGAACTCAATAGTAAAGGCTTCGATTACAACATGCTAGGTCTCTATATTAATGGA
321   T  S  N  E  E  L  N  S  K  G  F  D  Y  N  M  L  G  L  Y  I  N  G

CAGAATTGGAAAATTACCTCACTGACTCCGTACAATTTGCTTACTGCTTTAAAA
               Q  N  W  K  I  T  S  L  T  P  Y  N  L  L  T  A  L  K

1081 ACTGAATACCAAAGTTTACTGAAAATTACGAACCTTTTGCAAGAACTCGAGCCATCGAAATGCATA
361   T  E  Y  Q  S  L  L  K  I  T  N  L  L  Q  E  L  E  P  S  K  C  I

CTAGATTCCAAGTTTTTACTCAATAAGTTTTCTCAATTTTCATTGGGGAAGTTG
               L  D  S  K  F  L  L  N  K  F  S  Q  F  S  L  G  K  L

1201 CAAAACTTACAACCAATCAAAATGGATCTCCACACAATTCCAGGGTTCTCAGAATCAGTAATATAC
401   Q  N  L  Q  P  I  K  M  D  L  H  T  I  P  G  F  S  E  S  V  I  Y

TTCAATGATATCGAAAGCGACCCGCAATATGACGAATTAGTAAATAGTGTTCAA
               F  N  D  I  E  S  D  P  Q  Y  D  E  L  V  N  S  V  Q

1321 GCATTTTTTGATAAATCGAAATTCGGAGAGTTGCCTGAAATAAAGCAAAACTGGTCAGAGATCATA
441   A  F  F  K  K  S  K  F  G  E  L  P  E  I  K  Q  N  W  S  E  I  I

TTCGTTATAGATTTCGCCCGTTTAGAAGATAGTGAGGTGAAGGAGGCATTGGGT
               F  V  I  D  F  A  R  L  E  D  S  E  V  K  E  A  L  G
```

TABLE IV-continued
KRE5 sequence

```
1441 GGGTTGGTTCGTGCCGTTAATGTTGTCTCCCAGGGATATCCGCAAAGAGTCGGACTATTGCCATTT
 481  G  L  V  R  A  V  N  V  V  S  Q  G  Y  P  Q  R  V  G  L  L  P  F

AGTTCAGATAGTGACAAGTCCGTTGTTAATAAAATTTACGAGCTGAAGAACTCA
      S  S  D  S  D  K  S  V  V  N  K  I  Y  E  L  K  N  S

1561 ACTGACAATTTAACAGAATTAAAAAGTTTTTTGGAGACAATGCTGCTTGCAGATGGCCTTTCCGCG
 521  T  D  N  L  T  E  L  K  S  F  L  E  T  M  L  L  A  D  G  L  S  A

AATGCAAAACATTCAAAACACATACCAGTTCCAGATGTTTTCCATCTACTTGAT
      N  A  K  H  S  K  H  I  P  V  P  D  V  F  H  L  L  D

1681 GAACTTCAAATTGACGAAACATCAATTATAATCAATGGAGAGATTTACCCATTTAGAAAAAATTGG
 561  E  L  Q  I  D  E  T  S  I  I  I  N  G  E  I  Y  P  F  R  K  N  W

AATTATTTAATTGCAAAAGTTATCAAAAAGGACACTGAATTTATTCGTAAAGAA
      N  Y  L  I  A  K  V  I  K  K  D  T  E  F  I  R  K  E

1801 TTGAGCAATTCTTCTCCGAAAAACAAACAAATTAGCGTAAGGGACTTATTGCATTACAAATCTGCA
 601  L  S  N  S  S  P  K  N  K  Q  I  S  V  R  D  L  L  H  Y  K  S  A

AATCTGAGACATAATAAATATACACCAATTAATTTTGCTGATTCGGTATATTCT
      N  L  R  H  N  K  Y  T  P  N  Y  F  A  D  S  V  Y  S

1921 TCGGTCAACAATACTGCATTGGAAAGCGTATGCTCAGAAAGAATAGGCTACTATACTAAAAATGAA
 641  S  V  N  N  T  A  L  E  S  V  C  S  E  R  I  G  Y  Y  T  K  N  E

GAATACAATTTATTACACACAATCACATTAGTGGATGATTTTGGCTCTATTCAT
      E  Y  N  L  L  H  T  I  T  L  V  D  D  F  G  S  I  H

2041 GCTTTGAAAAGATTGAGAAACTTGTTGCATACTTCCTTTGTTGGTGTTAGGATCAGAATCATTCAC
 681  A  L  K  R  L  R  N  L  L  H  T  S  F  V  G  V  R  I  R  I  I  H

GTAGGTGATATTTCTGATATTTGGTATCAATTGCGTGGAAGTCTTTCCCAAAAA
      V  G  D  I  S  D  I  W  Y  Q  L  R  G  S  L  S  Q  K

2161 GATCCAATAGGCTCAATAAATACATTTATTGATGCTTTGAAACTTAAAAAGGTAAAAAGTCACACG
 721  D  P  I  G  S  I  N  T  F  I  D  A  L  K  L  K  K  V  K  S  H  T

TACAAAAAAAGCGGCTTAAACCAGTTAGGCCTTCATAAATGGCTTCCTGACATT
      Y  K  K  S  G  L  N  Q  L  G  L  H  K  W  L  P  D  I

2281 CCATTATTTGAATTGCAAAAGGGTTCATTTATTGCTTTGAACGGTAGATTTATCATCTTGATCAAA
 761  P  I  F  E  L  Q  K  G  S  F  I  A  L  N  G  R  F  I  I  L  I  K

ATGAAGTGCCAGAAACAGAACATTTCGAAGGCCAAAATCATAAAGAGAGAAGCT
      M  K  C  Q  K  Q  N  I  S  K  A  K  I  I  K  R  E  A

2401 CTAAGAACGATCGATTCAGTTTTCGCCCTAGATTTACTTTTTCCAGGTTTCTCACAGGAAATAATC
 801  L  R  T  I  D  S  V  F  A  L  D  L  L  F  P  G  F  S  Q  E  I  I

AATCCTGATTTGATAGAAATGATCTCCTCCATTTTAACTAGGTTGTTTTACCAA
      N  P  D  L  I  E  M  I  S  S  I  L  T  R  L  F  Y  Q

2521 GGTACACATATATACAATAATGGTATTGATTATACCACTGAAAGTAGCTTACCAAGAATGGATTTG
 841  G  T  N  I  Y  N  N  G  I  D  Y  T  T  E  S  S  L  P  R  N  D  L

AGCGAGTTTTTTAGACCTAATAATTTAACGATGTTTGAAGATGGAAAATCAGCT
      S  E  F  F  R  P  N  N  L  T  N  F  E  D  G  K  S  A

2641 TCTATTGATTTACTACTAATTTTAGATCCACTTGAAGAGAGAACGCAAATGATTCTTTCTCTTGTT
 881  S  I  D  L  L  L  I  L  D  P  L  E  E  R  T  Q  M  I  L  S  L  V

GAGCAATTCAGGCCTTTGAAATTTGTTAATATCCAGGTAATTTTAATGCCGACA
      E  Q  F  R  P  L  K  F  V  N  I  Q  V  I  L  N  P  T

2761 CTGGAATTAAACATTGTCCCTATTAAAGGAATATACGTTGATGACGCAGATATTGTCAAATCAATA
 921  L  E  L  N  I  V  P  I  R  R  I  Y  V  D  D  A  D  I  V  K  S  I
```

TABLE IV-continued
KRE5 sequence

```
                 ACTTCTGAGGATAGCAGATCAGATCCAGAAGTAGATATTGAAATGGATGTTCCT
                  T  S  E  D  S  R  S  D  P  E  V  D  I  E  M  D  V  P

2881 AATTCTTTCATTGTAGATAATAATTATCGGATAAAAAAATTGCTCATAGAATTACATTCCTTCTCT
 961  N  S  F  I  V  D  N  N  Y  R  I  K  K  L  L  I  E  L  H  S  F  S

AGCAAAACAGTCCTTTCAACTGGCAATATTGATGGTATGGGGGGTGTATGCCTA
                  S  K  T  V  L  S  T  G  N  I  D  G  N  G  G  V  C  L

3001 GCACTTGTCGATTCTGCAGGGAACATTATTGACAAAACTACAACAATGAAAACCTTTGGCTATGGA
1001  A  L  V  D  S  A  G  N  I  I  D  K  T  T  T  M  K  T  F  G  Y  G

CAATTTCATACCGACAAATTTTTAAAGGGTTGCTATATAAAAAGTTGTGATTCA
                  Q  F  N  T  D  K  F  L  K  G  C  Y  I  K  S  C  D  S

3121 AGATATACCGTTCAGTCATTTTCTACTGACGGGCATCCCGACTTTATACCATCAGATTCCTTGGAT
1041  R  Y  T  V  Q  S  F  S  T  D  G  N  P  D  F  I  P  S  D  S  L  D

ATACTGTCGTACAATCCACAAAAAATCGCTGTAAAAATTTCAGAAGAGCCTACA
                  I  L  S  Y  N  P  Q  K  I  A  V  K  I  S  E  E  P  T

3241 CACGAGGAAGATTACGAGGAAGGTCGCAACAATGATACAATAATCAATATTTTTACTATTTTAGAG
1081  N  E  E  E  Y  E  E  G  R  N  N  D  T  I  I  N  I  F  T  I  L  E

TCCGGGCCAGATGAGGAAGAGAGGTACATGCAAATGATTTTATCCATTTTGTCA
                  S  G  P  D  E  E  E  R  Y  M  Q  M  I  L  S  I  L  S

3361 AAGTGTCCCGAAACGCAAAAGGTGAATTTTTTCATTTTAGATCAGCCGTTTATCTCCGACACTTTA
1121  K  C  P  E  T  Q  K  V  N  F  F  I  L  D  Q  P  F  I  S  D  T  L

AGGAAATCATGTGAGTATATAAATTCCTCTGATGAAATGAGAGGCAATGTCATT
                  R  K  S  C  E  Y  I  N  S  S  D  E  N  R  G  N  V  I

3481 TTTTTGAATTATGAATGGCCTCAATGGTTAAGACCGCAAAGATTTTCTTCAAGGAGAAGGGATGTC
1161  F  L  N  Y  E  W  P  Q  W  L  R  P  Q  R  F  S  S  R  R  R  D  V

TCTAGATTTCTGTTCTTGGATGTCCTTTTACCTCAAAACATCTCCAAAGTGTTA
                  S  R  F  L  F  L  D  V  L  L  P  Q  N  I  S  K  V  L

3601 TATATGAGTCCAACTGAAGTACCGCTGGATCCTTTTGACATTTTTCAATTTCAAGGCCTCAAACGT
1201  Y  N  S  P  T  E  V  P  L  D  P  F  D  I  F  Q  F  Q  G  L  K  R

GCACCTCTAGGACTATTCCGAATGAGTGGTGATGGTTATTGGAAAGAAGGATAC
                  A  P  L  G  L  F  R  M  S  G  D  G  Y  W  K  E  G  Y

3720 TGGGAAAAAATGTTAAGGGAGAATAATTTAGAATTTTATTCTACCGAACCGGCCTTTTTAGTAAAC
1241  W  E  K  M  L  R  E  N  N  L  E  F  Y  S  T  E  P  A  F  L  V  N

TTAGAGAGGTTTCGGGAGTTAGATGCTGGTGATAAATACAGGATTCACTATCAA
                  L  E  R  F  R  E  L  D  A  G  D  K  Y  R  I  N  Y  Q

3841 CGTATTTCTACAGACGCCATGTCTCTTGTCAATATCGGCCAAGATCTAGTTAACAACCTACAACTC
1281  R  I  S  T  D  A  M  S  L  V  N  I  G  Q  D  L  V  N  N  L  Q  L

GAGGTTCCGATTAGGTTTCTCAAGGGATCGTATAAGAAGAAATTAGTTATTAAT
                  E  V  P  I  R  F  L  K  G  S  Y  K  K  K  L  V  I  N

3961 GATGAATGTGTTTCTGAATGGAAGAAAAAAATAAATAAGTTCGCATCCTCTCCTGGCGATGAAGAC
1321  D  E  C  V  S  E  W  K  K  K  I  N  K  F  A  S  S  P  G  D  E  D

GTACCTGGAGAAAGTGTTAGCAGCAAATACCAAGATTCCGACAATGCCGCTCCT
                  V  P  G  E  S  V  S  S  K  Y  Q  D  S  D  N  A  A  P

4081 CTGCATGACGAATTATAACTACTCCAGAAGAGTTCATTACGCGACTGTCCAAGAGCGTGAAGAATT
1361  L  H  D  E  L STOP

GCTTCTGCGCATAAGTCTTCTTCATAATAGATTTTTATATCATTTTTAGAACA
```

TABLE IV-continued

KRE5 sequence

4201 TAAAATTTCTCGCCAAGCTAGTTTTTTAGCTAAAAGCAGATATCCAGTAACATGGGTTCCGCTTTT
TGCAGCGAATACTATGAAGAGTTTTGCCCGACTGGCTCCCC

Gene Disruption

The genes were disrupted to get mutants totally lacking in gene function, such disruptants give a null phenotype which may be more severe than a mutant allele. This technique also demonstrates that these genes participate in a β-glucan assembly pathway.

a) Disruption of KRE1 locus

A null mutation of the KRE1 locus was generated by the one step gene disruption procedure using HIS3 as a selective marker (Rothstein, R. J., 1983, Meth. Enzymol., 101:202-211).

To create a kre1::HIS3 disruption construct, a HIS3 containing fragment was ligated into the SpeI and KpnI sites situated within the KRE1 coding sequence (Table II). The KRE1 BamHI-PstI fragment was introduced into an altered pUC19 plasmid, in which the KpnI site of the polylinker had been removed to create p411. Plasmid p411 was digested with Asp718 (an isoschizomer of KpnI), made blunt ended with Klenow fragment and then ligated with a nonphosphorylated XhoI linker (5'-CCCCTCGAGGGG-3'), to generate p458. The HIS3 gene could be isolated from PBSK:HIS3 as a SpeI-XhoI fragment and ligated into p458 also digested with SpeI and XhoI. The ligation product of this last reaction was called p463, digestion of p463 with NcoI and SphI, which cut within the KRE1 portion of the insert but not the HIS3 portion, allowed disruption of the KRE1 locus upon transformation.

The diploid TA405, homozygous for the his3 mutation was transformed with a restriction fragment of the cloned DNA containing a disruption of the KRE1 coding region. His+ tranformants were sporulated and subjected to tetrad analysis. Several independent transformants gave rise to two His+ kre− segregants and two His− Kre+ segregants (18 out of 18 tetrads analyzed). The killer resistant segregants consistently formed slightly smaller colonies upon spore germination when compared to the killer sensitive segregants, but individual cells were of normal size and morphology as judged by light microscopy. The structure of the integrated kre1::HIS3 deletion replacement was confirmed by Southern analysis of the chromosomal DNA from disrupted haploids.

Phenotype of the KRE1 disruptant

The levels of (1→6)-β-glucan were analyzed for the spore progeny of a tetrad, from the isogenic diploid TA405 made heterozygous for a kre1::HIS3 disruption mutation, (KRE1/kre::HIS3). Strains 463-1A and 463-1B display a reduced level of (1→6)-β-glucan and carry the kre1::HIS3 mutation. Disruption of the KRE1 locus of the haploid strain, 7B (glc1, ura3, his3), resulted in strain 3 (glc1, ura3, his3, kre1::HIS3).

Electron Microscopy Procedure

The conditions presented below represent a modified version of the procedure published by H. Zlotnik et al. (1984, J. Bateriol., 159:1018-1026). Cells were grown in minimal medium (Halvorson's salts as described previously) to stationary phase, harvested and washed with distilled water. Cell pellets were fixed in a solution containing 3% glutaraldehyde in 0.1M sodium phosphate buffer (pH 7.2) for 70 min. Following fixation, cell pellets were rinsed in buffer, then post-fixed for 1 hour in 1% OsO4 in 0.1M sodium phosphate buffer (pH 7.2) and then rinsed again. Cell pellets were subsequently dehydrated through a graded ethanol series, infiltrated and embedded in Spurr's expoxy resin (Spurr, A. R., 1969, J. Ultrastructure Res., 26:31-43). Gold- and silver-colored sections were mounted on formvar-coated grids and sections were stained with 2% aqueous uranyl acetate followed by Reynold's lead citrate (Reynold, E. S., 1963, J. Cell. Biol., 17:208-212). Sections were viewed on a Philips EM410® electron microscope at an operating voltage of 80 kV.

Electron Microscopy of kre1 Mutant Cell Walls

The kre1::HIS3 mutant yeast cells were examined by electron microscopy and compared to wild type cells. Under the conditions, employed wild type cells were found to have a finely delineated dark-staining outer layer. This layer was missing from kre1 mutant cells and the outer surface appeared rough in texture. The mutant cell wall material also stained more intensely, especially in the outer half of the wall. These structural alterations were found to segregate 2:2 in a tetrad obtained from a TA405 diploid made heterozygous for a kre1 disruption mutation (KRE1/kre1::HIS3).

b) Disruption of KRE5 locus

A null mutation at the KRE5 locus was created by one step gene replacement, using a kre5 deletion and HIS3 insertion construct and an integrative plasmid used directly to transform an isogenic diploid, TA405, to histidine prototrophy. In this construct the 3.0 kb EcoR1-BamH1 fragment of the KRE5 gene was replaced by a 1.8 kb fragment carrying the HIS3 gene from plasmid pBH1S31. The plasmid construct was digested with PvuII before transformation into TA405. His+ transformants were sporulated and segregants examined by tetrad analysis. Each disruption construct gave the same phenotype upon integration at the KRE5 locus. Analysis of 30 tetrads from transformants, YDK5, 7, 9, 11, 16 of TA405 revealed a 2:2 segregation in colony size with two wild type colonies and two microcolonies. Large colonies were His− and sensitive to killer toxin. Suppressors arose from the microcolonies at a frequency of 1 in $10^7$ to 1 in $10^8$ and such suppressors were selected for by continued growth of disruptants. Suppressors were invariably His+ and completely resistant to killer toxin. The structure of the integrated kre5 Δ::HIS3 construct was confirmed by Southern analysis of chromosomal DNA isolated from diploids heterozygous for the disruption. A single band of 12.5 kb was detected in the parent strain TA405 using a 3 kb EcoR1-BamH1 fragment of the cloned gene as a probe. Additional bands at 6.5 kb and 3.05 kb were detected in the His+ transformants, YDK7, 9, 11 and 16, consistent with a disruption at the predicted locus. To test allelism of the disruptant with the kre5-1 mutation, a random spore analysis of tetrads from K5D4, a cross between S726 and YDK5/3B, (kre5-1)

kre5Δ1::H1S3) was performed. All of 367 spore progeny examined were found to be resistant to killer toxin, indicating close linkage, and that the cloned gene was KRE5. To verify that the observed disruptant phenotype was due to disruption of the KRE5 gene, we tested the ability of the cloned KRE5 gene to complement kre5Δ1::H1S3. YDK9 was transformed with the wild type KRE5 on a centromeric plasmid and sporulated. Spores carrying both the chromosomal deletion (His+) and wild type KRE 5 on pRS315 (Leu+) were found to be wild for growth and confirmed that the severe growth defect observed was due to the specific disruption of the KRE5 gene.

Phenotype of the kre5 disruptant

The Hind III- SalI fragment of pKRE5, which contained the KRE5 gene, was subcloned into the yeast multi-copy vector pJDB207 to produce pKRE520. Transformation of a kre5 disruptant, YDK5/3B and a Kre+ strain (YDK5/1C), with pKRE520 did not increase the (1→6)-β-D-glucan levels above wild type (32.1+1/−5.6 μg mg-1 dry wt.). Also, when KRE5 and KRE1 were both overproduced, glucan levels were not increased above wild type. The (1→6)-β-D-glucan content of five independent disruptants harbouring second site suppressors was examined and found to be reduced to 1.9+/−0.4 μg mg-1 dry wt., compared to 34.6+/−0.4 μg mg-1 dry wt. for an otherwise Kre+ strain (YDK5/1C).

The residual glucan from one disruptant was examined in detail. Glucan from YDK5/3B was treated separately with α-amylase and non-lytic (1→6)-β-D-glucanase. Following dialysis, the amount of carbohydrate detected was not significantly reduced. The residual material is, therefore, unlikely to be glycogen or (1→6)-β-D-glucan. It is possibly a "limit" (1→3)-β-D-glucan, which is resistant to further digestion by zymolyase. Disaccharide analysis of hydrolysed glucan from a kre5 disruptant, YDK5/3B, did not detect any gentiobiose present in the sample (described previously). This suggested that the alkali-insoluble cell wall glucan remaining in a kre5 disruptant is completely lacking in (1→6)-β-D-glycosidic linkages.

Spores harbouring the KRE5 deletion were tested for osmotic fragility by dissection onto and growth on YEPD containing 1.2M sorbitol. Such treatment did not however alleviate the extremely slow growth of the disruptants. In addition, microscopic examination of disruptant cells in the presence of the vital stain methylene blue did not reveal an increase of lysed or dead cells. Cells deleted for KRE5 did, however, show gross morphological aberrations. Cells were clumped, often larger than wild type, contained more than one bud and appeared to show incomplete cell separation with cells inseparable by microdissection or sonication.

Discussion

We have cloned the KRE1 gene from *Saccharomyces cerevisiae* and shown that a disruption of the KRE1 locus results in an approximately 40% reduction of cell wall (1→6)-β-glucan. Haploid yeast strains with a disrupted kre1 allele grow somewhat more slowly than wild type and were found to have an unusual cell wall ultrastructure. Yeast cell wall (1→6)-β-glucan is a highly branched glucose polymer composed mostly of linear (1→6)-linked residues as well as some linear (1→3)-linked residues. Branching occurs through triply linked (1→3, 1→6)-β-glucopyranosyl residues. Structural analysis of the (1→6)-β-glucan, which remains in a kre1 mutant (mutant glucan) when compared to the glucan purified from isogenic wild type cells, showed that each glucan was composed of a similar set of linked residues. However, the mutant glucan contained fewer (1→6)-linked residues which were incorporated into a polymer of smaller average size. These results define at least a two step biosynthetic pathway for the production of cell wall (1→6)-β-glucan.

The KRE1 gene product (Kre1p) has a functional amino-terminal signal sequence that directs the protein into the yeast secretory pathway, where it is extensively modified probably through the addition of O-linked mannose residues. Yeast mating-type agglutinin protein (Lasky, R. D. & Ballou, C. E., 1988, *Proc. Natl., Acad. Sci. USA*, 85:349-353; Watzele, M. et al., 1988, *Eur. Mol. Biol. Organ.*, 7:1483-1488) and a large proportion of the bulk cell wall protein (Frevert, J. and Ballou, C. E., 1985, *Biochemistry*, 24:53-759) are serine threonine rich and O-glycosylated. Therefore, by analogy, Kre1p may also be localized at the yeast cell surface. In support of this idea, fusion constructs which place a leader-deleted KRE1 fragment next to the carboxy-terminus of the PHO5 open reading frame (Meyhack, B. et al., 1982, *Eur. Mol. Biol. Organ.*, 1:675-680), lead to a fusion protein which partially complements a kre1 mutant and directs acid phosphatase activity to the cell surface. The twenty-one carboxy-terminal amino acid residues of Kre1p form a hydrophobic sequence, which may serve as a membrane spanning domain or provide a signal for attachment of a glycosylphosphatidylinositol membrane anchor (Conzelmann, A. et al., 1988, *Eur. Mol. Biol. Organ.*, 7:2233-2240).

The appearance of kre1 disruptant cells, as examined using electron microscopy, revealed that the outer portion of the wall was abnormal. Particularly noticeable was the lack of a finely delineated dark staining region, thought to be a surface layer of mannoprotein (Zlotnik, H. et al., 1984, *J. Bacteriol.*, 159:1018-1026). This observation may have functional significance, as kre1 mutants over secrete proteins normally found in the growth medium (Bussey, H. et al., 1983, *Curr. Genetics*, 7:449-456). It is likely that wild type cells release a certain portion of wall-localized proteins into the growth medium and this process is exaggerated in kre1 mutant cells. In addition, the kre1 mutant cell walls were found to stain more intensely, especially in the outer half of the wall, leading to a bipartite appearance. This may suggest that a kre1 mutant is particularly defective in the assembly of the outer wall, which could be the region of (1→6)-β-glucan localization (Cabib, E. et al., 1982, *Ann. Rev. Biochem.*, 51:763-793).

A pathway of gene products necessary for yeast (1→6)-β-glucan biosynthesis is implicated by the finding that other mutants are resistant to killer toxin. Mutations at either the KRE5 or KRE6 loci result in killer resistance and a reduced amount of cell wall (1→6)-β-glucan. This reduction is not affected by a kre1 mutant allele suggesting that mutations at the KRE5 or KRE6 loci are epistatic to KRE1. Genetic analysis of kre5 and kre6 mutants suggests that they interact, and biochemical studies indicate that the products of these genes are involved in some early step necessary for glucan synthesis. Mechanistically, it seems reasonable that the KRE5 and KRE6 gene products could be required for the production of an acceptor glucan, which is defined by the (1→6)-β-glucan fraction that remains in a kre1 mutant. This interpretation implies that the mutant kre5-1 or kre6-1 alleles lead to the production of an altered acceptor glucan, which cannot be extended in a KRE1 dependent fashion and, therefore, result in killer toxin resistance. For KRE5, deletion of this gene led to the complete loss of detectable alkali-insouble (1→6)-β-D-glucan from cells. Such KRE5 deleted mutants had apparently normal levels of (1→3)-β-D-glucan, as was found for KRE1 deletion strains and kre6 mutants. This suggests that these gene products are on a pathway for (1→6)-β-D-glucan synthesis, and that such a pathway is distinct from that leading to (1→3)-β-D-glucan synthesis.

Cloning and sequence analysis of the KRE5 gene indicates that it encodes a large protein that is predicted to be a soluble ER resident glycoprotein containing the yeast ER retention signal. Although we do not know the exact function of the Kre5p, it clearly performs some early and apparently (1→6)-β-D-glucan specific event in the ER. This could be in the transport of a (1→6)-β-D-glucan substrate into the ER. We do not favour this idea for two reasons, the protein is not predicted to be membrane associated and does not appear to be defective in the synthesis of (1→3)-β-D-glucan or pleiotropic in its effects. The substrate for (1→6)-β-D-glucan synthesis is unknown, but is likely to be UDP-glucose (i.e. uridine diphosphate glucose), also the substrate for (1→3)-β-D-glucan (Kang, M. S. and Cabib, E., 1986, *Proc. Nat. Acad. Sci USA*, 83:5808–5812). One interesting possibility is that some core (1→6)-β-D-glucan is made in the ER, and that KRE5 and possibly KRE6 are directly involved in such core synthesis. There are clear precedents for such ER synthesis with glycoconjugants of proteins (Kornfeld, R. and Kornfeld, S., 1985, *Ann. Rev. Biochem.*, 54:631–664); in addition, in plants, cell wall xyloglucans are thought to be made in the Golgi and transferred to the cell surface (Moore, P. J. and Staehelin, L. A., 1988, *Planta*, 174:433–445). The core (1→6)-β-D-glucan found in KRE1 deleted strains and the mature (1→6)-β-D-glucan are both soluble polymers once digested free of the (1→3)-β-D-glucan to which they are attached in the cell wall. Thus, a soluble core (1→6)-β-D-glucan structure could traverse the yeast secretory pathway to the cell surface where it is elaborated in a KRE1-dependent manner by addition of (1→6)-β-D-glucan sidechains and cross-linked to the (1→3)-β-D-glucan in the cell wall.

The phenotype of the KRE5 deletion strain with extremely slow growth and aberrant cell morphology suggests that (1→6)-β-D-glucan is essential for the normal vegetative growth of yeast cells. The KRE5 defect is not osmoticically remedial, as strains harbouring a deleted KRE5 grow as slowly under iso-osmotic conditions in 1.2M sorbitol.

Figures 1A, 1B:
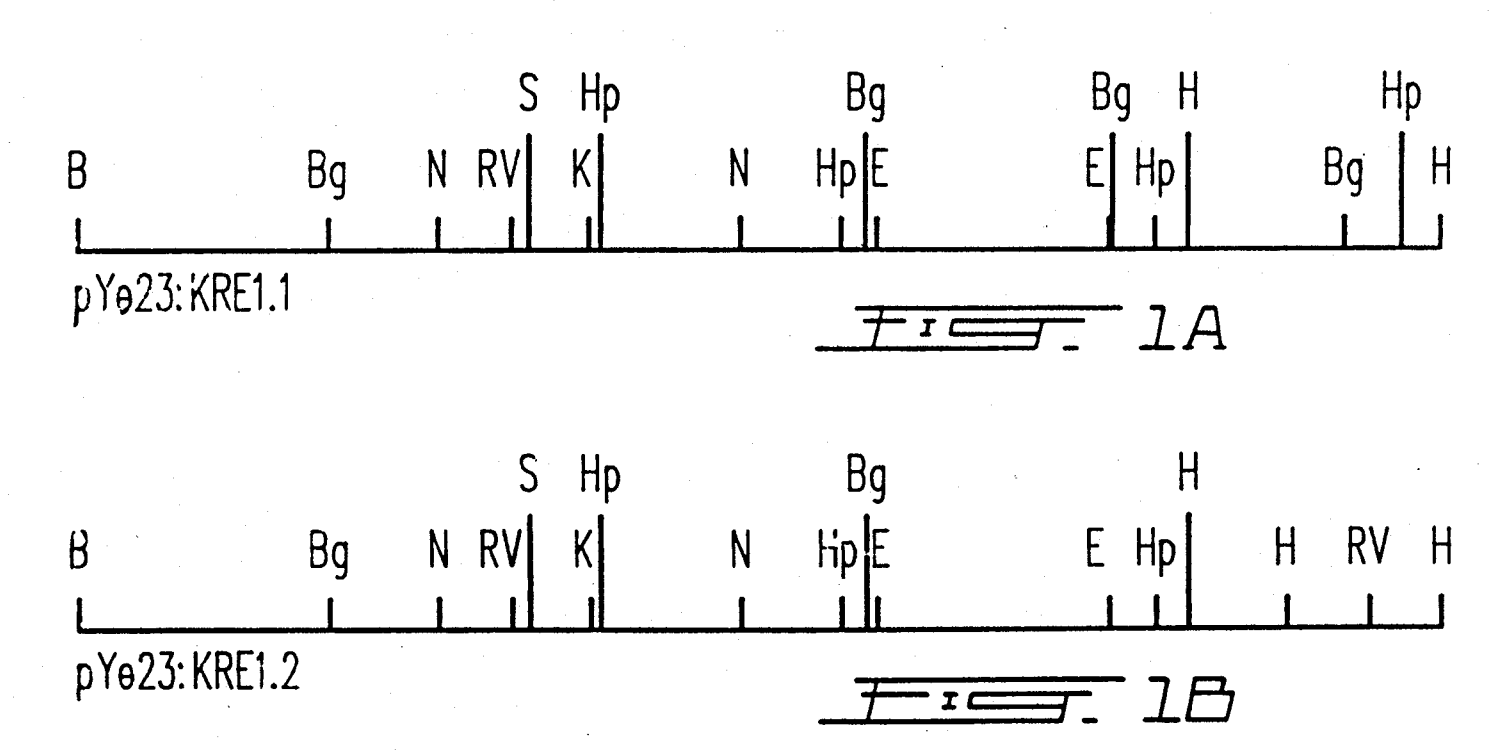

Cell wall (1→6)-β-glucan has been reported to occur among species from taxonomically diverse genera of yeasts including *Candida albicans* (Manners, D. J. et al., 1974, *J. Gen. Microbiol.*, 80:411–417). *C. albicans* is of particular interest because of its dimorphic nature and pathogenicity. Glucan accounts for 50–70% of the *C. albicans* cell wall and appears to function as the main structural component of both the yeast and mycelial forms (Fleet, G. H., 1985, *Current Topics in Medical Mycology*, 1:24–56). As was observed for *S. cerevisiae*, most of the cell wall glucan was isolated from whole cells as an alkali insoluble fraction which was found to contain two glucan subclasses. One glucan subclass closely resembled the *S. cerevisiae* (1→6)-β-glucan and while the other was found to contain relatively more (1→3)-linked glucopyranosyl residues, both types of glucan appear to be highly branched and composed predominantly of 1→6-linked residues (Gopal, P. K. et al., 1984, *J. Gen. Microbiol.*, 130:3295–3301). We have recently isolated two DNA fragments from the *C. albicans* genome capable of complementing the kre-phenotype of an *S. cerevisiae* kre1 mutant (FIGS. 1a and 1b).

It is likely that *C. albicans* homologs of the *S. cerevisiae* KRE genes described here, have a similar function in the biosynthesis of the *C. albicans* cell wall. However, the greater abundance of (1→6)-linked residues in the total cell wall glucan of *C. albicans* may imply that KRE homologs are associated with additional structural or morphological roles in this fungus. Partly because of the functional similarity of gene products required for most eukaryotic cellular processes, it has been difficult to devise specific antifungal antibiotics. Identification of the synthetic machinery for components, like fungal cell wall β-glucans, that are absent in mammalian cells, should reveal proteins that are excellent potential targets for specific antifungal inhibitors. The demonstration here that (1→6)-β-D-glucan synthesis is essential for normal cell growth indicates unequivocally, and for the first time, that inhibitors of this pathway would act as antifungals.

The following examples therefore, are not to be considered as limiting the preparation of any particular compound to the method described in the example as the examples are provided solely to illustrate the best modes currently known to applicants for the usage of the novel DNA sequences of this invention.

EXAMPLE I

Large Scale (1→6)-β-Glucan Preparation

Yeast (1→6)-β-glucan was isolated from a 2 litre culture of wildtype cells (strain 7B) or a 5 litre culture of kre1 mutant cells (strain 3), each grown to stationary phase in YEPD, 1X Halvorson's salts. The cells were harvested, washed with distilled water and stored at −70° C. Mannoprotein and alkali soluble glucan was removed via 5×100 ml extractions with 3% aqueous solution of NaOH, each for 1 hour at 70° C. Following alkali extraction, the cell walls were neutralized (with phosphate buffer pH 6.8) and digested with 33 mg of Zymolyase 100,000 ® in 10 mM sodium phosphate buffer pH 6.8 (with a 40 ml final volume containing 0.01% sodium azide) for 16 hours at 37° C. Following this digestion, insoluble material was removed by centrifugation (12,000 r.p.m.) and the supernatant treated with 20 μl amylase (10 mg/ml, Boehringer Manneheim Canada Ltd., Dorval, Que) for two hours at room temperature. After amylase treatment, the glucan containing solution was extracted 2× with 5 ml portions of phenol. Several 10 ml ether extractions removed residual phenol. The aqueous phase was collected and dialyzed against distilled water in Spectra/Por ® tubing with a 6,000–8,000 Mol. wt. cut off, for five hours, then freeze dried. The freeze dried material was solubilized in 5 ml of distilled water and further dialyzed in Spectra/Por ® tubing with a 2000 Mol. wt. cut off for 30 hours before a second freeze drying. The water soluble material which remains after this procedure was used for structural analysis. Two litres of a culture of wild type cells yielded 40–50 mg of (1→6)-β-glucan and five liters of a culture of kre1 mutant cells produced an equivalent amount.

Structural Analysis of (1→6)-β-Glucan from a kre1 Mutant

To facilitate $^{13}$C-NMR analysis of the (1→6)-β-glucan fraction isolated from a kre1::HIS3 disruption strain (mutant glucan), a large-scale procedure for the purification of approximately 50 mg of zymolyase resistant glucan was designed. The yeast strain 7B (his3 ura3 glc1) used for wild type glucan purification carried the glc1 mutation to minimize glycogen contamination (Tkacz, J. S., 1984, *Microbial Cell Wall Synthesis and Autolysis*, 287-295); disruption of the KRE1 locus in this strain created a kre1 null mutant, (strain 3), with a reduced amount of (1→6)-β-glucan (Table V).

TABLE V (1→6)-β-glucan levels in kre1 mutant strains

| Yeast Strain | Allele at KRE1 locus | (1→6)-β-glucan μg/mg dry wt. |
|---|---|---|
| 463-1A | kre1::HIS3 | 24.9 ± 3.5 |
| 463-1B | kre1::HIS3 | 19.3 ± 2.0 |
| 463-1C | KRE1+ | 34.2 ± 3.2 |
| 463-1D | KRE1+ | 34.5 ± 0.6 |
| 7B | KRE1+ | 27.0 ± 0.8 |
| 3 | kre1::HIS3 | 17.2 ± 2.2 |

$^{13}$C Nuclear Magnetic Resonance Spectroscopy $^{13}$C-NMR spectra were obtained using 10 mm diameter tubes, with 40 mg of glucan dissolved in 3 ml D$_2$O. Data were collected under conditions of proton decoupling, using a WH 400 Bruker spectrometer at 100.62 MHz, with a sweep width of 6493.5 Hz and an acquisition time of 0.631 s. The pulse angel was 73° and the pulse interval was 4.0 s, during which the decoupler was gated off. The probe temperature was maintained at 19° C. Each spectrum was recorded several times, from independent glucan samples, with approximately 10,000 scans. The reference for the chemical shift values was external dioxane at 67.4 ppm.

The proton decoupled $^{13}$C-NMR spectrum of glucan purified from the wild type strain (7B) is obtained under conditions where the signal area reflects relative amounts of the constituent carbon atom(s) (Shimamura, A., 1989, *Carbohydr. Res.*, 185:239-248). The wild type glucan showed predominant signals at 103.8, 76.4, 75.7, 73.8, 70.3 and 69.6 ppm for C-1, C-3, C-5, C-2, C-4 and C-6 respectively. These chemical shifts are characteristic of linear (1→6)-β-glucan (Gopal, P. K. et al., 1984, *J. Gen. Microbiol.*, 130:3295-3301; Bassieux, D. et al., 1977, *Carbohydr. Res.*, 56:19-33; Saito, H. et al., 1977, *Carbohydr. Res.*, 58:293-305). Several minor signals can be ascribed to the presence of linear (1→3)-linked, branched (1→3,1→6)-linked and terminal β-glucopyranosyl residues in the polymer. For example, the signal with a chemical shift of 61.5 ppm is the result of residues unsubstituted at C-6, as found for terminal β-glucopyranosyl residues or those which have a linear (1→3)-linked structure. Integration analysis suggests that 82% of the residues are O-substituted at the C-6 position.

Each of the signals of the proton decoupled $^{13}$C-NMR spectrum of glucan purified from the kre1 mutant strain (3) is found to have a signal of equivalent chemical shift present in the spectrum of wild type glucan. Therefore, each glucan contains a similar set of linked residues. A noticeable difference between the two spectra is the relative ratio of signals within a given spectrum. The spectrum of the mutant glucan contains a higher proportion of signals corresponding to linear (1→3)-linked, branched and terminal β-glucopyranosyl residues than the wildtype. Integration analysis shows that 64% of the residues are O-substituted at C-6.

Hence both the mutant and wild type glucans give rise to $^{13}$C-NMR spectra consistent with a branched (1→6)-β-glucan structure. The mutant glucan differs from the wild type in having fewer residues O-substituted at C-6. These results were confirmed by methylation analysis which also indicated that the reduction of C-6, O-substituted residues was due to fewer linear (1→6)-linked glucopyranosyl units.

Gel Filtration Chromatography

A Sepharose CL-6B ® (Pharmacia) column of dimensions 110.0 cm × 1.0 cm was used at a flow rate of 16 ml/hour. The eluent was 0.1M aqueous solution of NaOH and 0.4 ml fractions were collected. Calibration of the column was carried out using blue dextran (Pharmacia) to indicate the void volume and several dextrans of known molecular weights (Sigma). Determination of the carbohydrate content of each fraction was carried out by the phenolsulfuric acid method (Dubois, M. et al., 1956, *Anal. Chem.*, 28:350-356).

Gel filtration chromatography of mutant and wild type glucans over a Sepharose CL-6B ® column demonstrated that the mutant glucan had a smaller average degree of polymerization than the wild type. The wild type glucan displayed a range of different sized material, with an average predicted molecular weight of 40 kD. The mutant glucan displayed a range of material with smaller predicted molecular weights and an average of 20 kD. These results suggest that the average degree of polymerization of the wild type glucan was approximately 200, while that of the mutant glucan was about 100.

EXAMPLE II

Killer resistant mutants have reduced levels of cell wall (1→6)-β-glucan, and identify a pathway of genes required for β-glucan production Mutants in three complementation groups were found to have reduced levels of cell wall (1→6)-β-glucan (Table VI). The level in strain S708, which harbors the kre1-3 allele, was reduced 40% in agreement with the previous observations for mutants containing kre1-1 or a kre1::HIS3 disruption mutation. Strains S726 and S731 carrying mutations at the KRE5 and KRE6 loci respectively showed a significant reduction in (1→6)-β-glucan and demonstrated a slow growth phenotype which cosegregated with the killer resistance when compared to wild type strains or the kre1 mutant, S708. The level of (1→6)-β-glucan was not altered in the kre2 strain S706 (Table VI).

TABLE VI (1→6)-β-glucan levels of kre-strains

| Yeast Strain | KRE allele | (1→6)-β-glucan μg/mg dry wt. |
|---|---|---|
| S442 | KRE+ | 29.4 ± 2.0 |
| S484 | KRE+ | 30.7 ± 1.3 |
| S708 | kre1-3 | 16.1 ± 3.3 |
| S706 | kre2-2 | 26.3 ± 2.1 |
| S726 | kre5-1 | 11.6 ± 1.5 |
| S731 | kre6-1 | 11.9 ± 0.5 |

Cell wall (1→6)-β-glucan levels were determined for killer resistant mutants isolated in the S442 and S484 genetic background. Total alkali insoluble glucan was not significantly different for any of these strains (with an average of 134±28 μg/mg dry wt.) except for S726 which showed a modest increase (175.2±6.8 μg/mg dry wt.).

Double mutants were constructed for the strains that showed a reduced level of cell wall (1→6)-β-glucan. The level of (1→6)-β-glucan in double mutants of kre1 with kre5 or kre6 was not significantly lower than that found in kre5 or kre6 single mutants. This result suggests that mutations at both the kre5 and kre6 loci lead to killer toxin resistance because they are epistatic to KRE1 and suggests that they function earlier in glucan synthesis than the KRE1 gene product.

Interaction of kre5 and kre6 Mutants

To explore these probable earlier steps in glucan synthesis, we examined the properties of kre5, kre6 double mutants (See Table VII below). These double mutants show more extreme phenotypes than those of either mutant singly, having further reduced levels of β-D-(1→6)-glucan and slower rates of vegetative growth.

TABLE VII

| | kre5-1 and kre6-1 double mutants | | |
|---|---|---|---|
| Strain YEPD | Genotype | (1→6)-β-D-glucan level μg/mg dry weight | Colony size 6 days on at 30° C. |
| S442 | KRE5 KRE 6 parent strain | 39.0 ± 4.4 | 5 mm |
| HAB 224-2C | kre5-1 | 19.0 ± 1.0 | 2 mm |
| HAB 223-2B | kre6-1 | 22.0 ± 1.0 | 4 mm |
| HAB 225-18A | KRE5 KRE 6 | 41.7 ± 3.0 | 5 mm |
| HAB 225-18B | kre5-1 kre6-1 | 11.8 ± 1.2 | ~1 mm |
| HAB 225-18C | kre5-1 kre6-1 | 12.0 ± 0.5 | ~1 mm |
| HAB 225-18D | KRE5 KRE 6 | 38.1 ± 5.0 | 5 mm |

EXAMPLE III

Isolation of functional homologs of KRE similar genes from pathogenic fungi

The kre mutants allow isolation of similar genes by functional complementation from pathogenic fungi. These pathogenic fungi are the targets for potential antifungal agents.

A KRE1 homolog from Candida albicans was obtained by complementation of a kre1 mutant of Saccharomyces cerivisiae.

The C. albicans genomic library, used for complementation of the kre- phenotype of strain 11A (kre1.1 ura3), was contained on pEMBLY23 (Baldari and Cesareni, 1985, Gene, 35:27-32). The restriction map of the inserts (9.5 kb) of two complementing plasmids, designated pYe23:KRE1.1 and pYe23:KRE1.2, are shown in FIG. 1 (inserts are designated by the plasmid name). The restriction maps of these inserts are similar but differ in restriction polymorphisms and can be distinguished by the relative number of the following restriction sites: H, Bg, RV and Hp. Restriction sites abbreviations are as follows: BamHI (B), BglII (Bg), EcoRI (E), EcoRV (RV), HindIII (H), HpaI (Hp), K (KpnI), NsiI (N), SalI (S). This information is consistent with these complementing plasmids containing alleles of this region from the diploid Candida albicans. (Ph.D. thesis, Department of Biology, McGill University, July 1989, C. Boone, "Characterization of the KRE1 gene of Saccharomyces cerevisiae and its role in (1→6)-β-D-glucan production".

In addition, the cloned KRE genes allow isolation of KRE genes from other organisms, such as fungi pathogenic on plants or animals, by the techniques of reverse genetics. For example, antibodies can be raised against KRE gene products following expression of such by gene fusion approaches, and injection of such KRE gene products into rabbits and obtaining the antisera in standard ways. Such antibodies can then be used to screen expression libraries of pathogenic fungi such as C. albicans, for expression of KRE homologs that immunologically cross react with antibodies to the S. cerevisiae KRE gene products.

EXAMPLE IV

Overproduction or modulation of glucan structure by under or overexpression of KRE genes or their homologs from other species This section offers a methodology or means to control the amount of β-glucan, and the nature of the polymer made. This methodology offers a rational approach to the design of unique β-glucan polymers which may be of great potential value to the chemical, medical and food industries.

As demonstrated for kre1, 5 and 6 mutants, reduced expression of these gene products results in altered glucan structure and reduced amounts of β-glucan. By overexpression of KRE1, 5 and 6 in yeast from appropriate multicopy vectors, or with strong promoters, that is by overproducing the components of the β-glucan synthetic pathway, it is reasonable to expect to overproduce β-glucan. In addition, by varying the proportions of the components of the synthetic pathway, it should also be feasible to vary the structure of the β-glucan polymer produced. For example, if genes such as KRE5 and KRE6 were overexpressed more than KRE1, then the proportion of β-glucan backbone to (1→6)-β-D-glucan side chains would be altered.

In another example, the structure of the C. albicans (1→6)-β-D-glucan outer chain is different from that in S. cerevisiae. By expressing the C. albicans KRE1 homolog in a S. cerevisiae strain deleted for KRE1, a hybrid glucan will be made with the S. cerevisiae glucan backbone and the C. albicans outer chain.

Other examples would be to alter the properties of the proteins encoded by the KRE1, 5 and 6 genes so that they have altered Km's for substrates, such mutants made through standard genetic engineering methods may compete more or less avidly with (1→3)-glucan synthesizing enzymes and change the proportion of (1→3) to (1→6)-β-D-glucans made in the yeast cells, thus making altered glucan polymers with different properties.

EXAMPLE V

'In vivo' Screening methods for specific antifungal agents

Having yeast strains with and without (1→6)-glucan permits a differential screen for compounds that inhibit (1→6)-glucan synthesis. Specifically, kre5 mutant strains or kre5 suppressor strains such as YDK5/3B, contain no (1→6)-glucan; wildtype strain TA405, or isogenic haploids derived from it, have (1→6)-glucan. Compounds from natural sources (for example, from fermentation broths of microorganisms), or from chemical synthesis can be tested for their ability to inhibit or prevent growth of TA405 while having no affect on the kre5 suppressor strain. Compounds which show such differential inhibition would be specific inhibitors of (1→6)-glucan synthesis and could be evaluated further as specific antigungal compounds.

As an example, the fungal inhibitor, Aculeacin A, a proposed (1→3) glucan inhibitor (Yamaguchi, H. et al., 1985, *Microbiol. Immunol.*, 29:609–623) was tested. This compound at 0.5 micrograms/ml inhibited the growth of both the parent TA405, an isogenic haploid YDK5/1C and the kre5 suppressor strain YDK5/3B, when present in YEPD agar plates incubated at 30° C. Similarly, the protein synthesis inhibitor cycloheximide at 1.3 micrograms/ml in YEPD agar inhibited both the parent and (1→6)-glucan defective strain. These examples illustrate that the suppressor strain is not differentially susceptible to these non (1→6)-glucan specific compounds.

EXAMPLE VI

'In vitro' Screening methods for specific antifungal agents

The invention provides a DNA sequence which specifies a protein, Kre5p. Using the techniques of yeast molecular biology (Botstein, D., and Fink, G. R., 1988, *Science*, 240:1439–1433), it is possible to identify this protein and determine its function. The Kre5p protein when expressed in an expression system can be purified (for example by purification using an antibody raised against a synthetic peptide based on the KRE5 sequence). The purified Kre5p could be screened for compounds that would interact with it. Such Kre5p could also be examined for possible 'in vitro' function in (1→6)-glucan synthesis. Such a function when determined would also allow for 'in vitro' screening for compounds that inhibited such activity. Inhibitors or compounds that interacted with Kre5p would be candidates for antifungal agents.

EXAMPLE VII

Structurally modified yeast glucans

Glucans obtained from alkali-extracted cell walls of kre1 mutants or disruptants, from kre5 mutants or disruptants harbouring suppressors, or from kre6 mutants, are structurally different from wall glucans previously described in that they differ in various ways in the amount or type of (1→6)-β-D-linked-glucan in the polymer. Because of such altered structures, it is likely that the altered glucans will be polymers with different solubility, rheological and viscoelastic properties. As yeast glucans are used as food additives or as thickeners and stabilizers of gels, suspensions and in emulsions, (Seeley, R. D., Robbins E. A., Sucher, R. W., Schuldt, E. H., Newell, J. A., Sidoti, D. R., and Clayton, R. A., 1974, *Proceedings 4th Int. Congress Food Science and Technology*, 5:135–141; Seeley, R. D., 1977, *MBAA Technical Quarterly*, 14:35–39; Robbins, E. A., Seeley, R. D., U.S. Pat. No. 4,122,196, Yeast glycan production from yeast cells.); or in medicine as immunomodulators and in plants as elicitors of defense reactions.

These modified glucans or others made by altering the KRE1, 5 or 6 genes are new products that may have new properties and roles in these and other processes.

1-Strains hypersensitive to zymolyase facilitate protein recovery from yeasts

Mutants of kre1, kre5 and kre6 are more sensitive to zymolyase digestion of their cell walls than their wildtype parent. $1 \times 10^7$ cells per ml of strains S442, S484, S708 kre1-3, S726 kre5-1, S731 kre6-1, were incubated with 16.7 Units/ml of zymolyase (60,000 Units/g) in 0.067M sodium phosphate pH 7.0 for 60 min. at 30° C. Cell survival for wildtype strains S442 and S484 was 2%, for kre1-3, 0.1%; for kre5-1 and kre6-1 0.003%. These mutant strains could be used to more readily lyse yeast cells, thus enabling yeast or heterologous proteins expressed in yeast to be released. Such protein extracts from these mutant yeasts could be used directly or as a preparation from which proteins can be purified.

2-Immunomodulators

B-glucans with (1→6)-linkages from fungi including *Saccharomyces cerevisiae* are used as immunomodulators to stimulate the immune and phagocytosis systems of mammals and man (DiLuzio, N. P., Hoffmann, E. O., Cook, J. A., Browder, W., Mansell, P. W. A., 1977, *In Control of Neoplasia by Modulation of the Immune System*, Edited by Chirigos, M. A. Raven Press, p. 475,; Czop, J. K., 1986., *Advances in Immunology*, 38:361–398). The invention provides means to structurally modify or overproduce such B-glucan immunomodulators through use of mutants or through expression or alteration of the KRE genes. Overproduced glucans or modified glucans with different properties such as solubility may be more potent immunomodulators or have different or more specific responses in man. These glucans could be obtained and used medically for immunostimulation, for example, in the treatment of cancer or of infections.

EXAMPLE VIII

Stimulation of Plant defense responses by β-glucans

Mixed linked (1→6), (1→3)-β-glucans from fungi including *Saccharomyces cerevisiae* stimulate a host defense response in plants, (Ryan, C. A., 1987, *Ann. Rev. Cell Biol.*, 3:295–317. Hahn, M. G., Albersheim, P., 1978, *Plant Physiol.*, 62:107–111). These B-glucans are termed elicitors and stimulate the synthesis of plant compounds called phytoalexins which can inhibit a wide range of microorganisms and protect the plant from pathogenic infection. This invention provides a means to modify or overproduce such β-glucan elicitors through use of kre mutants or through expression or modification of the cloned KRE genes. Overproduced or modified glucans can be obtained in this way, the latter may be more potent elicitors or have a different spectrum of response on crop plants and could be used on crop plants including trees to elicit phytoalexin production as a prophylactic for prevention of plant disease from microbial or fungal infection or through toxicity to insects or other animals feeding on such stimulated plant tissues.

EXAMPLE IX

A general method to select for yeast mutants resistant to yeast killer toxins

Seeded Plate Assay for Killer Resistance

Yeast strains were grown to stationary phase in liquid media (under plasmid selective conditions if necessary) and 30 μl of this culture was used to inoculate 10 ml of minimal media, 1% agar, 1× Halvorson's pH 4.7. Concentrated toxin, 7 μl of 1000× concentrated media from S14a/T158C (Bussey, H. et al., 1983, *Curr. Genetics*, 7:449–456) was introduced onto the solidified agar and the plates incubated at 18° C. overnight, followed by a 30° C. incubation for 24 hours.

Isolation of Killer Resistant Mutants

To isolate mutants resistant to K1 killer toxin, $1 \times 10^7$ cells of S486 or S484 were mixed with $2 \times 10^8$ of a nonreverting, homozygous leu2 K1+ diploid strain and plated on complete media lacking leucine pH 4.7. After eight days, colonies of resistant S486 and S484 could be seen above a lawn of initially plated cells. The colonies were purified and tested for resistance by replica plating onto methylene blue medium (0.003% methylene blue) which had just been inoculated with diploid K1 killer cells (approximately 1×10⁷ cells spread onto the agar surface and allowed to dry). After incubation for one to two days at 25° C., resistant colonies were white or light blue (depending on the particular mutant allele), while sensitive colonies were dark blue.

Killer Resistant Mutants Identify a Group of Genes Required for Cell Wall (1→6)-β-Glucan Production Resistant mutants were characterized by performing genetic analysis in an isogenic background. Six complementation groups were defined by recessive mutations each of which segregated as a defect in a single gene. Two of the complementation groups were found to be equivalent to KRE1 and KRE2 described by K. Al-Aidroos & H. Bussey (1978, *Can. J. Microbiol.*, 24:228-237). The other complementation groups designated KRE4, KRE5, KRE6 and KRE8 are novel. Segregation analysis indicated that the kre1, 2, 5 and 6 mutations identify four separate loci.

This method differs from other previously described methods in allowing slow growing mutants to be selected and should be generally applicable to the selection of useful mutants resistant to killer toxins. The method essentially exposes toxin sensitive yeast cells to the presence of killer toxin, under conditions where the toxin producing cells cannot grow. Sensitive cells are killed by this treatment; but cells that have acquired resistance mutations can grow and are thus selected. Such mutants are allowed to grow and form colonies on a solid agar surface. Allowing growth on a solid surface permits poorly growing mutants to be obtained. They are not outgrown by faster growing mutants, which is a key step in the method. Such slow growing mutants are likely partially defective in the synthesis of essential components of the yeast cell surface through leaky mutations in genes essential for fungal growth; kre5-1 and kre6-1 mutants were obtained in this way. This methodology is applicable to selecting yeast mutants resistant to other killer toxins. These resistant mutants may identify new genes whose products are required for fungal growth and are thus useful targets for antifungal agents. In addition, such mutants may permit manipulation of other molecules in the yeast cell wall. In addition, some of the kre mutants may affect the cell membrane and/or other cellular compartments.

Many killer toxins are knwon (Young, T. W., 1987, *The Yeasts*, 2nd edition, 2:131-164, editors Rose, A. H. & Harrison, J. S., Academic Press, London); most are proteins or glycoproteins, but the mechanism of their action is often unknown. Mutants resistant to these or other toxins can be obtained by this selection method with, in some cases, the simple modification of using toxin extracts free of yeast cells instead of a mutant non-growing killer strain, as described in the selection method.

While the invention has been described in connection with specific embodiments thereof, it will be understood that it is capable of further modifications, and this application is intended to cover any variations, uses, or adaptations of the invention following, in general, the principles of the invention and including such departures form the present disclosure, as come within known or customary practice within the art to which the invention pertains, and as may be applied to the essential features hereinbefore set forth, and as follows, in the scope of the appended claims.

I claim:

1. Isolated DNA which codes for a gene which participates in a yeast cell wall β-glucan assembly pathway, of Saccharomyces cerevisiae, wherein the sequence of said DNA is selected from the group consisting of:

```
                              KRE1
           NheI
           GCTAGCAGTTATTTCACTTTCATT

TACAGCATCCCTCATGTTTATTATCTTCTT

TATCTAATATAAATTAGGAACTAAATAAT          -360

CCCCTCACCGTATAAAGCGACAGTTCCGTG

ACGGTTACTATTATGAATATCTCAACGGAA

AGAGGGCATTAAAAGATCATAATAGTTGGT

ACTCTCGTATTTTATATATATATATCACT          -240

ATATTTTAACACTTTTACTGCTCAATTGTG

CCATATACTTCGCCTTATTGCGTACATTCT

TCACCTTGTATCCCCCTACCTCAGCGTGTA

EcoRV
TGGTGATATCGCGTTTTTTCATAAACTGA          -120

GAATGGGGCTTTTTCTATAACGTGTATTAT

GAAAAAAAGAAAATAAAAATCAAGAATTAA

GCACTTGTATATGCTACAGTAAAGACCTCT

TCAACTTCTGCAAGACAATCAAAAAAAAA            -1

ATG ATG CGT CGC ACG CTA TTA CAT
Met Met Arg Arg Thr Leu Leu His

TCA TTC GCT ACG CTG CTA CTT TCT
Ser Phe Ala Thr Leu Leu Leu Ser
                                ▽   •
TTG TCG TTG TGG TCA GCT GCG GTC
Leu Ser Leu Trp Ser Ala Ala Val
            ▽
ATG GCA GCT GTG ACA ACT         90
Met Ala Ala Val Thr Thr         30

CAG GTT ACA GTG GTA ACA AAT GTC
Gln Val Thr Val Val Thr Asn Val

ACC GCT CAA ACA GGT TTC TTC ACT
Thr Ala Gln Thr Gly Phe Phe Thr

ACG GTA TTC ACT ACC ACT AAC GAT
Thr Val Phe Thr Thr Thr Asn Asp
----  ----------  ------

GTC GGA ACC ACC GTC ACT CTT ACT
Val Gly Thr Thr Val Thr Leu Thr
----  ----------------------

HincII
CAG ACA GTC AAC AGA GCC         270
Gln Thr Val Asn Arg Ala          90
-------
```

```
ACT ATG CTA CCA ACC ACG ACG ACT
Thr Met Leu Pro Thr Thr Thr Thr

TCT ACC TCA TCT ACT GGT AAG ACA
Ser Thr Ser Ser Thr Gly Lys Thr

ACC ACC ACT GTT CCT ACC GCA ACT
Thr Thr Thr Val Pro Thr Ala Thr

TCA TCG TTG TCT TCG GGA         360
Ser Ser Leu Ser Ser Gly         120

CTG TAT TTA TCT ACA GTT ACC ACG
Leu Tyr Leu Ser Thr Val Thr Thr
.........

KpnI
ACA AAC GAT TTG GGT ACC ACA GTT
Thr Asn Asp Leu Gly Thr Thr Val
.........................

ACA TTG ACT CAA ACG TTC ACA CAT
Thr Leu Thr Gln Thr Phe Thr His
.................

TCT AGC ACC AGT GCT ACT         450
Ser Ser Thr Ser Ala Thr         150

TCA TCC GCC TCC TCG TCT GTG TCC
Ser Ser Ala Ser Ser Ser Val Ser

TCG TCT GTA TCT TCG TCT GGT TCA
Ser Ser Val Ser Ser Ser Gly Ser

TCC TCC AGT GTA AAG ACG ACC ACA
Ser Ser Ser Val Lys Thr Thr Thr

TCG ACA GGG AGC GCA GTA         540
Ser Thr Gly Ser Ala Val         180

GCT GAA ACA GGC ACC AGG CCA GAC
Ala Glu Thr Gly Thr Arg Pro Asp

CCC TCC ACA GAC TTC ACA GAA CCT
Pro Ser Thr Asp Phe Thr Glu Pro

SpeI
CCT GTG TCT GCT GTC ACT AGT CTA
Pro Val Ser Ala Val Thr Ser Leu

TCT ATT GAC TCA TAC ATT         630
Ser Ile Asp Ser Tyr Ile         210

ACC ATC ACT GAA GGT ACA ACC TCC
Thr Ile Thr Glu Gly Thr Thr Ser

ACT TAC ACA ACC ACA CGT GCG CCA
Thr Tyr Thr Thr Thr Arg Ala Pro

ACG TCC ATG TGG GTC ACT GTT GTT
Thr Ser Met Trp Val Thr Val Val

AGA CAG GGC AAC ACT ATC         720
Arg Gln Gly Asn Thr Ile         240

ACT GTG CAA ACT ACT TTT GTC CAG
Thr Val Gln Thr Thr Phe Val Gln

SnaBI
CGT TTC TCC TCC CAG TAC GTA ACA
Arg Phe Ser Ser Gln Tyr Val Thr

GTC GCT TCT CCC TCC GTG GGG TCT
Val Ala Ser Pro Ser Val Gly Ser

ATT GGG ATG GGT ACT TTA         810
Ile Gly Met Gly Thr Leu         270

ACC GGT ACT GTA GGC GTT ATT AAA
Thr Gly Thr Val Gly Val Ile Lys

TCT GCA ATA AAG AAA ACA GTT TCG
Ser Ala Ile Lys Lys Thr Val Ser

CAT AAT GAG GCC CAG CAT CTA GGT
His Asn Glu Ala Gln His Leu Gly
........

ATG AGT TCG TTT ACT TCA         900
Met Ser Ser Phe Thr Ser         300
................

ATT TTG GGT GGG CTA TTA ACG GTT
Ile Leu Gly Gly Leu Leu Thr Val
.........................

TTA ATT TGG TTC TTA TAA ATTTTA
Leu Ile Trp Phe Leu
.................

TTCAGAAATAAACACAAACATATACATATAT

AAGAGTAAAAATAAAAAAATAAAAA        1005
                                 313

AATTTTACAGGGTTAAAAATAAAGAAAACCA

TCACTCCTTTTCTATTTCATAATCCATGACA

NsiI
AACTTGATGCAT                     1079;

and

KRE5

-77             TATATAACGTGGCA

TATTAAAGATTAATTGTCCTGGTAGAATATAG

ACGTATCAGTGTGAGTGCCTCTGTTGATTA

1  ATGAGACTACTTGCGTTGGTATTGTT
   1  M  R  L  L  A  L  V  L  L

ATTGTTGTGTGCGCCGCTTCGTGCATGGACTT
L  L  C  A  P  L  R  A  W  T

ATAGCTTACGATATGGCATACCCGAATCTGCT
Y  S  L  R  Y  G  I  P  E  S  A

CAGGTCTGGTCTATTTTAGTTCATTTACTG
Q  V  W  S  I  L  V  H  L  L

121  GGCGATGTTGATAATCAGCTGTTAAC
   41   G  D  V  D  N  Q  L  L  T

TAATTTATATCCTTTGGTTACCGGTTTGGATG
N  L  Y  P  L  V  T  G  L  D

ACGAGATTGATATTCAAGAAAATCTTGTGGCG
D  E  I  D  I  Q  E  N  L  V  A

CTAACTTCCAATGTATTAAGGGAGCGATAC
L  T  S  N  V  L  R  E  R  Y

241  GATAAAGAGGATGTGGCTGATTTATT
   81   D  K  E  D  V  A  D  L  L
```

```
GGAACTGTATGCTAGTCTTTACCCTATGGGTA
  E  L  Y  A  S  L  Y  P  M  G

TGATACAGCACGATATCAGTTCCAATGCAGAA
  M  I  Q  H  D  I  S  S  N  A  E

CAAGACGATGCAAATAGTAGCTATTTCGTT
  Q  D  D  A  N  S  S  Y  F  V

361    TTGAATGGTAATAGGTACGAAAAGCC
    121    L  N  G  N  R  Y  E  K  P

CGACGACGTGTTCTACTTGAAATCTAAGGATT
  D  D  V  F  Y  L  K  S  K  D

TAACAATTCAACAGAAAGTCCCAGATGTTGAT
  L  T  I  Q  Q  K  V  P  D  V  D

GTTATACAACCTTACGATGTTGTCATTGGT
  V  I  Q  P  Y  D  V  V  I  G

481    ACTAACTCAGAAGCGCCGATATTGAT
    161    T  N  S  E  A  P  I  L  I

CTTGTACGGTTGTCCTACCGTTATTGACTCCG
  L  Y  G  C  P  T  V  I  D  S

ACTTCGAAGAATTCAATAGGAATTTATTTATG
  D  F  E  E  F  N  R  N  L  F  H

GAAGCAATGAATGGAGAGGGAAAATTTAGA
  E  A  M  N  G  E  G  K  F  R

601    TTTATTTGGAGATCCACATGTTCCCT
    201    F  I  W  R  S  T  C  S  L

TGATGGGAAAAGCGTGGAGTATCCCTTAACTC
  D  G  K  S  V  E  Y  P  L  T

ATCCGCTTGAAATTACTTTAGAAAATGGTTCT
  H  P  L  E  I  T  L  Q  N  G  S

AGAATGAGCTCCATACCTCAATTAAAAAAA
  R  M  S  S  I  P  Q  L  K  K

721    ATACTATATACTGTACCCAAAGAAAT
    241    I  L  Y  T  V  P  K  E  I

ATTGGTTGGAGCAGACAACGATGATCAGCTCC
  L  V  G  A  D  N  K  K  Q  L

ATGATCTAGAACCAGAAGAATTACGTGAACTT
  H  D  L  E  P  E  E  L  R  E  L

GATTTGAGAGTAACATCGTTAATCTCAGAA
  K  L  R  V  T  S  L  I  S  E

841    TTTTACCAATATAAAAAGGATATCAC
    281    F  Y  Q  Y  K  K  D  I  T

AGCCACTCTAAATTTCACCAAAAGTATTGTTA
  A  T  L  N  F  T  K  S  I  V

ACAACTTTCCACTAATCTCTAAACAACTGATT
  N  N  F  P  L  I  S  K  Q  L  I

AAGGTTTCATCTGTTAACAAGGATATAATA
  K  V  S  S  V  N  K  D  I  I

961    ACAAGTAATGAAGAACTCAATAGTAA
    321    T  S  N  E  E  L  N  S  K

AGGCTTCGATTACAAGATGCTAGGTCTCTATA
  G  F  D  Y  N  M  L  G  L  Y

TTAATGGACAGAATTGGAAAATTACCTCACTG
  I  N  G  Q  N  W  K  I  T  S  L

ACTCCGTACAATTTGCTTACTGCTTTAAAA
  T  P  Y  N  L  L  T  A  L  K

1081   ACTGAATACCAAAGTTTACTGAAAAT
    361    T  E  Y  Q  S  L  L  K  I

TACGAACCTTTTGCAAGAACTCGAGCCATCGA
  T  N  L  L  Q  E  L  E  P  S

AATGCATACTAGATTCCAAGTTTTTACTCAAT
  K  C  I  L  D  S  K  F  L  L  N

AAGTTTTCTCAATTTTCATTGGGGAAGTTG
  K  F  S  Q  F  S  L  G  K  L

1201   CAAAACTTACAACCAATCAAAATGGA
    401    Q  N  L  Q  P  I  K  M  D

TCTCCACACAATTCCAGGGTTCTCAGAATCAG
  L  H  T  I  P  G  F  S  E  S

TAATATACTTCAATGATATCGAAAGCGACCCG
  V  I  Y  F  N  D  I  E  S  D  P

CAATATGACGAATTAGTAAATAGTGTTCAA
  Q  Y  D  E  L  V  N  S  V  Q

1321   GCATTTTTGATAAATCGAAATTCGG
    441    A  F  F  D  K  S  K  F  G

AGAGTTGCCTGAAATAAAGCAAAACTGGTCAG
  E  L  P  E  I  K  Q  N  W  S

AGATCATATTCGTTATAGATTTCGCCCGTTTA
  E  I  I  F  V  I  D  F  A  R  L

GAAGATAGTGAGGTGAAGGAGGCATTGGGT
  E  D  S  E  V  K  E  A  L  G

1441   GGGTTGGTTCGTGCCGTTAATGTTGT
    481    G  L  V  R  A  V  N  V  V

CTCCCAGGGATATCCGCAAAGAGTCGGACTAT
  S  Q  G  Y  P  Q  R  V  G  L

TGCCATTTAGTTCAGATAGTGACAAGTCCGTT
  L  P  F  S  S  D  S  D  K  S  V

GTTAATAAAATTTACGAGCTGAAGAACTCA
  V  N  K  I  Y  E  L  K  N  S

1561   ACTGACAATTTAACAGAATTAAAAAG
    521    T  D  N  L  T  E  L  K  S

TTTTTTGGAGACAATGCTGCTTGCAGATGGCC
  F  L  E  T  M  L  L  A  D  G

TTTCCGCGAATGCAAAACATTCAAAACACATA
  L  S  A  N  A  K  H  S  K  H  I

CCAGTTCCAGATGTTTTCCATCTACTTGAT
  P  V  P  D  V  F  H  L  L  D

1681   GAACTTCAAATTGACGAAACATCAAT
    561    E  L  Q  I  D  E  T  S  I

TATAATCAATGGAGAGATTTACCCATTTAGAA
  I  I  N  G  E  I  Y  P  F  R

AAAATTGGAATTATTTAATTGCAAAAGTTATC
  K  N  W  N  Y  L  I  A  K  V  I

AAAAAGGACACTGAATTTATTCGTAAAGAA
```

```
                                              842   G  T  H  I  Y  N  N  G  I

TGATTATACCACTGAAAGTAGCTTACCAAGAA
       K   K   D   T   E   F   I   R   K   E    D   Y   T   T   E   S   S   L   P   R

1801  TTGAGCAATTCTTCTCCGAAAAACAA             TGGATTTGAGCGAGTTTTTTAGACCTAATAAT
 601   L   S   N   S   S   P   K   N          M   D   L   S   E   F   F   R   P   N   N

ACAAATTAGCGTAAGGGACTTATTGCATTACA            TTAACGATGTTTGAAGATGGAAAATCAGCT
  Q   I   S   V   R   D   L   L   H   Y       L   T   M   F   E   D   G   K   S   A

AATCTGCAAATCTGAGACATAATAAATATACA            2641  TCTATTGATTTACTACTAATTTTAGA
  K   S   A   N   L   R   H   N   K   Y   T    881   S   I   D   L   L   I   L   D

CCAAATTATTTTGCTGATTCGGTATATTCT              TCCACTTGAAGAGAGAACGCAAATGATTCTTT
  P   N   Y   F   A   D   S   V   Y   S        P   L   E   E   R   T   Q   M   I   L

1921  TCGGTCAACAATACTGCATTGGAAAG            CTCTTGTTGAGCAATTCAGGCCTTTGAAATTT
 641   S   V   N   N   T   A   L   E   S        S   L   V   E   Q   F   R   P   L   K   F

CGTATGCTCAGAAAGAATAGGCTACTATACTA            GTTAATATTCAGGTAATTTTAATGCCGACA
  V   C   S   E   R   I   G   Y   Y   T        V   N   I   Q   V   I   L   M   P   T

AAAATGAAGAATACAATTTATTACACACAATC
  K   N   E   E   Y   N   L   L   H   T   I   2761  CTGGAATTAAACATTGTCCCTATTAG
                                               921   L   E   L   N   I   V   P   I   R

ACATTAGTGGATGATTTTGGCTCTATTCAT              AAGAATATACGTTGATGACGCAGATATTGTCA
  T   L   V   D   D   F   G   S   I   H        R   I   Y   V   D   D   A   D   I   V

2041  GCTTTGAAAAGATTGAGAAACTTGTT            AATCAATAACTTCTGAGGATAGCAGATCAGAT
 681   A   L   K   R   L   R   N   L   L        K   S   I   T   S   E   D   S   R   S   D

GCATACTTCCTTTGTTGGTGTTAGGATCAGAA            CCAGAAGTAGATATTGAAATGGATGTTCCT
  H   T   S   F   V   G   V   R   I   R        P   E   V   D   I   E   M   D   V   P

TCATTCACGTAGGTGATATTTCTGATATTTGG
  I   I   H   V   G   D   I   S   D   I   W   2881  AATTCTTTCATTGTAGATAATAATTA
                                               961   M   S   F   I   V   D   N   N   Y

TATCAATTGCGTGGAAGTCTTTCCCAAAAA              TCGGATAAAAAAATTGCTCATAGAATTACATT
  Y   Q   L   R   G   S   L   S   Q   K        R   I   K   K   L   L   I   E   L   H

2161  GATCCAATAGGCTCAATAAATACATT            CCTTCTCTAGCAAAACAGTCCTTTCAACTGGC
 721   D   P   I   G   S   I   N   T   F        S   F   S   S   K   T   V   L   S   T   G

TATTGATGCTTTGAAACTTAAAAAGGTAAAA             AATATTGATGGTATGGGGGGTGTATGCCTA
  I   D   A   L   K   L   K   K   V   K        N   I   D   G   M   G   G   V   C   L

GTCACACGTACAAAAAAAGCGGCTTAAACCAG            3001  GCACTTGTCGATTCTGCAGGGAACAT
  S   H   T   Y   K   K   S   G   L   N   Q   1001   A   L   V   D   S   A   G   N   I

TTAGGCCTTCATAAATGGCTTCCTGACATT              TATTGACAAAACTACAACAATGAAAACCTTTG
  L   G   L   H   K   W   L   P   D   I        I   D   K   T   T   T   M   K   T   F

2281  CCATTATTTGAATTGCAAAAGGGTTC            GCTATGGACAATTTCATACCGACAAATTTTTA
 761   P   L   F   E   L   Q   K   G   S        G   Y   G   Q   F   H   T   D   K   F   L

ATTTATTGCTTTGAACGGTAGATTTATCATCT            AAGGGTTGCTATATAAAAAGTTGTGATTCA
  F   I   A   L   N   G   R   F   I   I        K   G   C   Y   I   K   S   C   D   S

TGATCAAAATGAAGTGCCAGAAACAGAACATT            3121  AGATATACCGTTCAGTCATTTTCTAC
  L   I   K   M   K   C   Q   K   Q   N   I   1041   R   Y   T   V   Q   S   F   S   T

TCGAAGGCCAAAATCATAAAGAGAGAAGCT              TGACGGGCATCCCGACTTTATACCATCAGATT
  S   K   A   K   I   I   K   R   E   A        D   G   H   P   D   F   I   P   S   D

2401  CTAAGAACGATCGATTCAGTTTTCGC            CCTTGGATATACTGTCGTACAATCCACAAAAA
 801   L   R   T   I   D   S   V   F   A        S   L   D   I   L   S   Y   N   P   Q   K

CCTAGATTTACTTTTTCCAGGTTTCTCACAGG            ATCGCTGTAAAAATTTCAGAAGAGCCTACA
  L   D   L   L   F   P   G   F   S   Q        I   A   V   K   I   S   E   E   P   T

AAATAATCAATCCTGATTTGATAGAAATGATC
  E   I   I   N   P   D   L   I   E   M   I   3241  CACGAGGAAGAATACGAGGAAGGTCG
                                              1081   H   E   E   E   Y   E   E   G   R

TCCTCCATTTTAACTAGGTTGTTTTACCAA
  S   S   I   L   T   R   L   F   Y   Q       CAACAATGATACAATAATCAATATTTTTACTA
                                                N   N   D   T   I   I   N   I   F   T

2521  GGTACACATATATACAATAATGGTAT
```

```
TTTTAGAGTCCGGGCCAGATGAGGAAGAGAGG
 I  L  E  S  G  P  D  E  E  E  R

TACATGCAAATGATTTTATCCATTTTGTCA
 Y  M  Q  M  I  L  S  I  L  S

3361  AAGTGTCCCGAAACGCAAAAGGTGAA
1121   K  C  P  E  T  Q  K  V  N

TTTTTTCATTTTAGATCAGCCGTTTATCTCCG
 F  F  I  L  D  Q  P  F  I  S

ACACTTTAAGGAAATCATGTGAGTATATAAAT
 D  T  L  R  K  S  C  E  Y  I  N

TCCTCTGATGAAATGAGAGGCAATGTCATT
 S  S  D  E  M  R  G  N  V  I

3481  TTTTGAATTATGAATGGCCTCAATG
1161   F  L  N  Y  E  W  P  Q  W

GTTAAGACCGCAAAGATTTTCTTCAAGGAGAA
 L  R  P  Q  R  F  S  S  R  R

GGGATGTCTCTAGATTTCTGTTCTTGGATGTC
 R  D  V  S  R  F  L  F  L  D  V

CTTTTACCTCAAAACATCTCCAAAGTGTTA
 L  L  P  Q  N  I  S  K  V  L

3601  TATATGAGTCCAACTGAAGTACCGCT
1201   Y  M  S  P  T  E  V  P  L

GGATCCTTTTGACATTTTTCAATTTCAAGGCC
 D  P  F  D  I  F  Q  F  Q  G

TCAAACGTGCACCTCTAGGACTATTCCGAATG
 L  K  R  A  P  L  G  L  F  R  M

AGTGGTGATGGTTATTGGAAAGAAGGATAC
 S  G  D  G  Y  W  K  E  F  Y

3720  TGGGAAAAAATGTTAAGGGAGAATAA
1241   W  E  K  M  L  R  E  N  N

TTTAGAATTTTATTCTACCGAACCGGCCTTTT
 L  E  F  Y  S  T  E  P  A  F

TAGTAAACTTAGAGAGGTTTCGGGAGTTAGAT
 L  V  N  L  E  R  F  R  E  L  D

GCTGGTGATAAATACAGGATTCACTATCAA
 A  G  D  K  Y  R  I  H  Y  Q

3841  CGTATTTCTACAGACGCCATGTCTCT
1281   R  I  S  T  D  A  M  S  L

TGTCAATATCGGCCAAGATCTAGTTAACAACC
 V  N  I  G  Q  D  L  V  N  N

TACAACTCGAGGTTCCGATTAGGTTTCTCAAG
 L  Q  L  E  V  P  I  R  F  L  K

GGATCGTATAAGAAGAAATTAGTTATTAAT
 G  S  Y  K  K  K  L  V  I  N

3961  GATGAATGTGTTTCTGAATGGAAGAA
1321   D  E  C  V  S  E  W  K  K

AAAAATAAATAAGTTCGCATCCTCTCCTGGCG
 K  I  N  K  F  A  S  S  P  G

ATGAAGACGTACCTGGAGAAAGTGTTAGCAGC
 D  E  D  V  P  G  E  S  V  S  S

AAATACCAAGATTCCGACAATGCCGCTCCT
 K  Y  Q  D  S  D  N  A  A  P

4081  CTGCATGACGAATTATAACTACTCCA
1361   L  H  D  E  L  STOP

GAAGAGTTCATTACGCGACTGTCCAAGAGCGT

GAAGAATTGCTTCTGCGCATAAGTCTTCTTCC

ATAATAGATTTTTATATCATTTTTAGAACA

4201  TAAAATTTCTCGCCAAGCTAGTTTTT

TAGCTAAAAGCAGATATCCAGTAACATGGGTT

CCGCTTTTTGCAGCGAATACTATGAAGAGTTT

TGCCCGACTGGCTCCCC.

* * * * *
```